US011471121B2

(12) United States Patent
Matsuda

(10) Patent No.: US 11,471,121 B2
(45) Date of Patent: Oct. 18, 2022

(54) RADIOGRAPHY APPARATUS, METHOD FOR OPERATING RADIOGRAPHY APPARATUS, AND PROGRAM FOR OPERATING RADIOGRAPHY APPARATUS

(71) Applicant: FUJIFILM CORPORATION, Tokyo (JP)

(72) Inventor: Hidenori Matsuda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 158 days.

(21) Appl. No.: 16/953,344

(22) Filed: Nov. 20, 2020

(65) Prior Publication Data
US 2021/0196223 A1 Jul. 1, 2021

(30) Foreign Application Priority Data

Dec. 27, 2019 (JP) .............................. JP2019-239132

(51) Int. Cl.
*A61B 6/00* (2006.01)
*G06T 5/00* (2006.01)
*G01R 31/36* (2020.01)
*G06F 3/14* (2006.01)

(52) U.S. Cl.
CPC .............. *A61B 6/54* (2013.01); *A61B 6/5258* (2013.01); *A61B 6/56* (2013.01); *G01R 31/3647* (2019.01); *G06T 5/002* (2013.01); *G06T 5/009* (2013.01); *G06F 3/14* (2013.01); *G06T 2207/10116* (2013.01)

(58) Field of Classification Search
CPC . A61B 6/542; A61B 6/586; A61B 2506/0276; A61B 2506/0209; H05G 1/56; H05G 1/10
See application file for complete search history.

(56) References Cited

U.S. PATENT DOCUMENTS 8,767,919 B2 * 7/2014 Nishino ............... A61B 6/4007
378/62

FOREIGN PATENT DOCUMENTS

JP 2019-005073 A 1/2019

* cited by examiner

*Primary Examiner* — Don K Wong
(74) *Attorney, Agent, or Firm* — Solaris Intellectual Property Group, PLLC

(57) ABSTRACT

The radiography apparatus is driven by power supplied from the battery. In the radiography apparatus, a radiation source that emits radiation to a subject, a radiation detector that receives the radiation transmitted through the subject and outputs a radiographic image, and an image processing device that performs image processing on the radiographic image are integrated. A CPU of the image processing device acquires a remaining level of the battery. The CPU performs control to operate both a first processing block that performs a noise suppression process and a visibility improvement process as first image processing and a second processing block that performs a density correction process as second image processing in a case in which the remaining level of the battery is equal to or greater than a threshold value. In contrast, in a case in which the remaining level of the battery is less than the threshold value, the CPU performs control to stop an operation of the first processing block and to operate only the second processing block.

10 Claims, 25 Drawing Sheets

<IN CASE IN WHICH REMAINING BATTERY LEVEL IS LESS THAN THRESHOLD VALUE>

RADIOGRAPHY APPARATUS, METHOD FOR OPERATING RADIOGRAPHY APPARATUS, AND PROGRAM FOR OPERATING RADIOGRAPHY APPARATUS

CROSS-REFERENCE TO RELATED APPLICATIONS

The present application claims priority under 35 U.S.C. § 119 to Japanese Patent Application No. 2019-239132, filed on Dec. 27, 2019. The above application is hereby expressly incorporated by reference, in its entirety, into the present application.

BACKGROUND

1. Technical Field

The technology of the present disclosure relates to a radiography apparatus, a method for operating the radiography apparatus, and a program for operating the radiography apparatus.

2. Description of the Related Art

JP2019-005073A discloses a radiography apparatus in which a radiation source that emits radiation to a subject, a radiation detector that receives the radiation transmitted through the subject and outputs a radiographic image, and an image processing device that performs image processing on the radiographic image are integrated. The radiography apparatus described in JP2019-005073A is driven by power supplied from a battery.

SUMMARY

In the battery-driven radiography apparatus disclosed in JP2019-005073A, there is a concern that the battery will run out, imaging will be stopped, and imaging efficiency will be significantly reduced. Therefore, it is important to take measures to make the battery last as long as possible.

In general, a sleep mode is adopted as the measures to make the battery last long. In the sleep mode, the supply of power to, for example, the radiation detector is temporarily stopped in a case in which radiation is not emitted for a predetermined period.

As described above, the sleep mode is a measure in a case in which radiation is not emitted, that is, in a case in which radiography is not performed. Therefore, in order to make the battery last longer, it is necessary to take measures to prevent a reduction in the capacity of the battery during radiography.

A technique which stops the operation of some of processing blocks performing image processing is considered as the measure to prevent a reduction in the capacity of the battery during radiography. However, in a case in which a mistake is made in selecting the processing block to be stopped, there is a concern that a radiographic image that is not suitable for observation will be generated.

An object of the technology of the present disclosure is to provide a radiography apparatus, a method for operating the radiography apparatus, and a program for operating the radiography apparatus which can make a battery last long while securing a radiographic image that is suitable for observation.

In order to achieve the above object, according to the present disclosure, there is provided a radiography apparatus that is driven by power supplied from a battery. The radiography apparatus comprises: a radiation source that emits radiation to a subject; a radiation detector that receives the radiation transmitted through the subject and outputs a radiographic image; and an image processing device that performs image processing on the radiographic image. The radiation source, the radiation detector, and the image processing device are integrated. The image processing includes first image processing that performs at least one of a noise suppression process suppressing noise of the radiographic image or a visibility improvement process improving visibility of the radiographic image and second image processing that performs a density correction process correcting densities of two or more radiographic images of the same subject which have a time difference therebetween. The radiography apparatus includes at least one processor. The processor acquires a remaining level of the battery, performs control to operate both a first processing block performing the first image processing and a second processing block performing the second image processing in a case in which the remaining level is equal to or greater than a predetermined threshold value, and performs control to stop an operation of the first processing block and to operate only the second processing block in a case in which the remaining level is less than the threshold value.

Preferably, the processor outputs the radiographic image from the radiation detector at a predetermined frame interval, and the density correction process is a process that stabilizes the density of the radiographic image of each frame.

Preferably, the processor performs control to display information indicating that the first image processing is not performed in a case in which the operation of the first processing block is stopped.

Preferably, the radiography apparatus has a first path from the radiation detector to the second processing block through the first processing block and a second path from the radiation detector to the second processing block without passing through the first processing block. Preferably, the processor performs control to select the first path in a case in which the remaining level is equal to or greater than the threshold value and performs control to select the second path in a case in which the remaining level is less than the threshold value.

Preferably, in a case in which the remaining level is less than the threshold value, the processor stops the supply of the power from the battery to the first processing block to stop the operation of the first processing block.

Preferably, the first processing block includes a logic circuit and the processor stops a switching operation of the logic circuit to stop the operation of the first processing block in a case in which the remaining level is less than the threshold value.

Preferably, the first processing block includes a memory that requires a refresh to replenish charge stored in a memory cell and temporarily stores intermediate data generated by processing and the processor directs an external circuit to perform the refresh in a case in which the remaining level is equal to or greater than the threshold value and directs the memory to perform the refresh in a case in which the remaining level is less than the threshold value.

Preferably, in a case in which the emission of the radiation is not performed for a predetermined period, the processor performs control to stop the operation of the first processing block and to operate only the second processing block, regardless of the remaining level.

According to the present disclosure, there is provided a method for operating a radiography apparatus that is driven by power supplied from a battery and includes a radiation source that emits radiation to a subject, a radiation detector that receives the radiation transmitted through the subject and outputs a radiographic image, and an image processing device that performs image processing on the radiographic image, the radiation source, the radiation detector, and the image processing device being integrated. The image processing includes first image processing that performs at least one of a noise suppression process suppressing noise of the radiographic image or a visibility improvement process improving visibility of the radiographic image and second image processing that performs a density correction process correcting densities of two or more radiographic images of the same subject which have a time difference therebetween. The method comprises: an acquisition step of acquiring a remaining level of the battery; a first operation control step of performing control to operate both a first processing block performing the first image processing and a second processing block performing the second image processing in a case in which the remaining level is equal to or greater than a predetermined threshold value; and a second operation control step of performing control to stop an operation of the first processing block and to operate only the second processing block in a case in which the remaining level is less than the threshold value.

According to the present disclosure, there is provided a program for operating a radiography apparatus that is driven by power supplied from a battery and includes a radiation source that emits radiation to a subject, a radiation detector that receives the radiation transmitted through the subject and outputs a radiographic image, and an image processing device that performs image processing on the radiographic image, the radiation source, the radiation detector, and the image processing device being integrated. The image processing includes first image processing that performs at least one of a noise suppression process suppressing noise of the radiographic image or a visibility improvement process improving visibility of the radiographic image and second image processing that performs a density correction process correcting densities of two or more radiographic images of the same subject which have a time difference therebetween. The program causes a computer to function as: an acquisition unit that acquires a remaining level of the battery; and an operation control unit that performs control to operate both a first processing block performing the first image processing and a second processing block performing the second image processing in a case in which the remaining level is equal to or greater than a predetermined threshold value, and performs control to stop an operation of the first processing block and to operate only the second processing block in a case in which the remaining level is less than the threshold value.

According to the technology of the present disclosure, it is possible to provide a radiography apparatus, a method for operating the radiography apparatus, and a program for operating the radiography apparatus which can make a battery last long while securing a radiographic image that is suitable for observation.

BRIEF DESCRIPTION OF THE DRAWINGS

Exemplary embodiments according to the technique of the present disclosure will be described in detail based on the following figures, wherein:

FIG. 22A illustrates the image processing unit in a case in which the operation control signal illustrated in FIG. 20 is received, and FIG. 22B illustrates the image processing unit in a case in which the operation control signal illustrated in FIG. 21 is received;

DETAILED DESCRIPTION

First Embodiment

Figure 1:
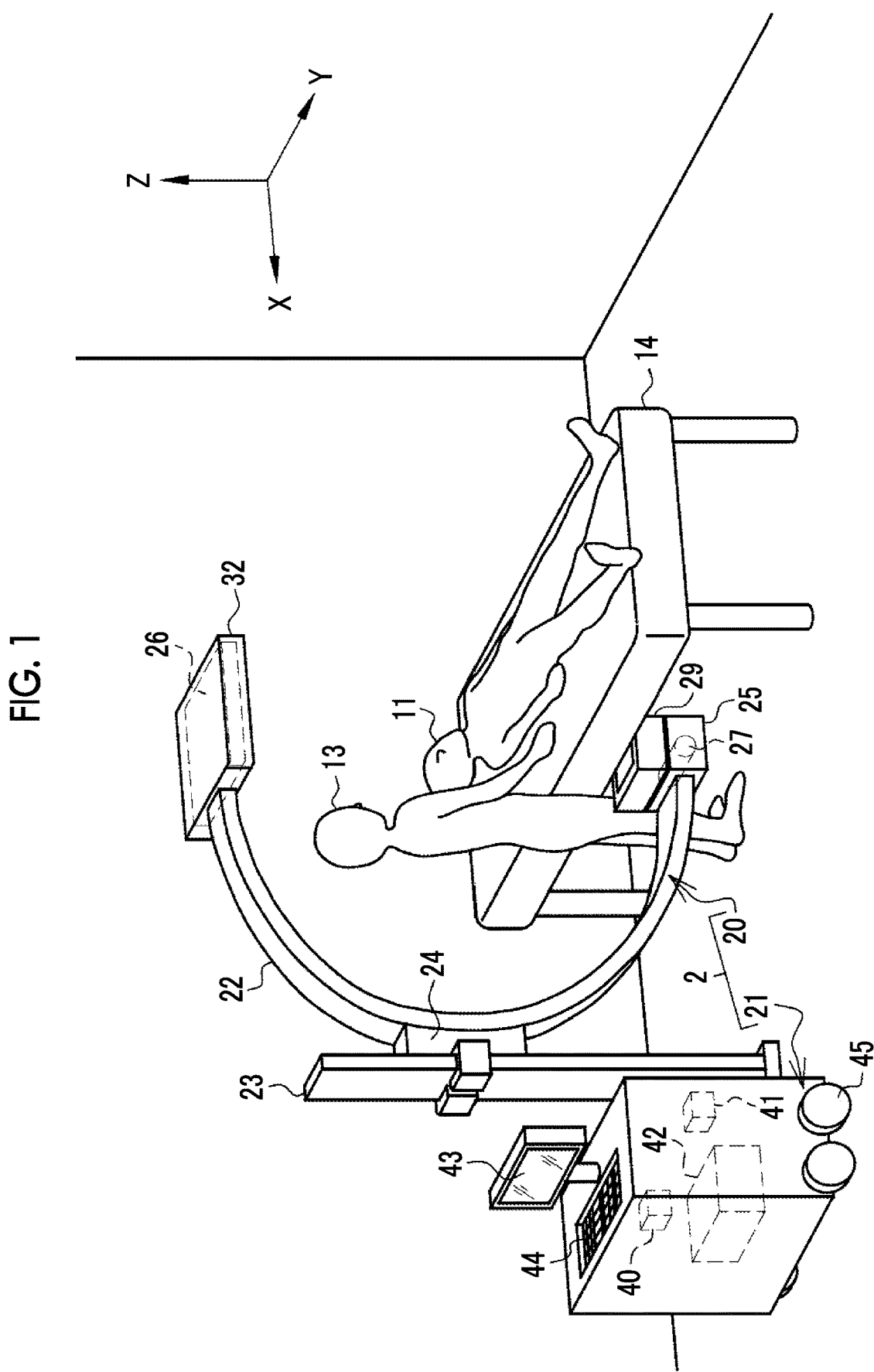
FIG. 1 is a diagram illustrating a radiography apparatus.
Figure 2:
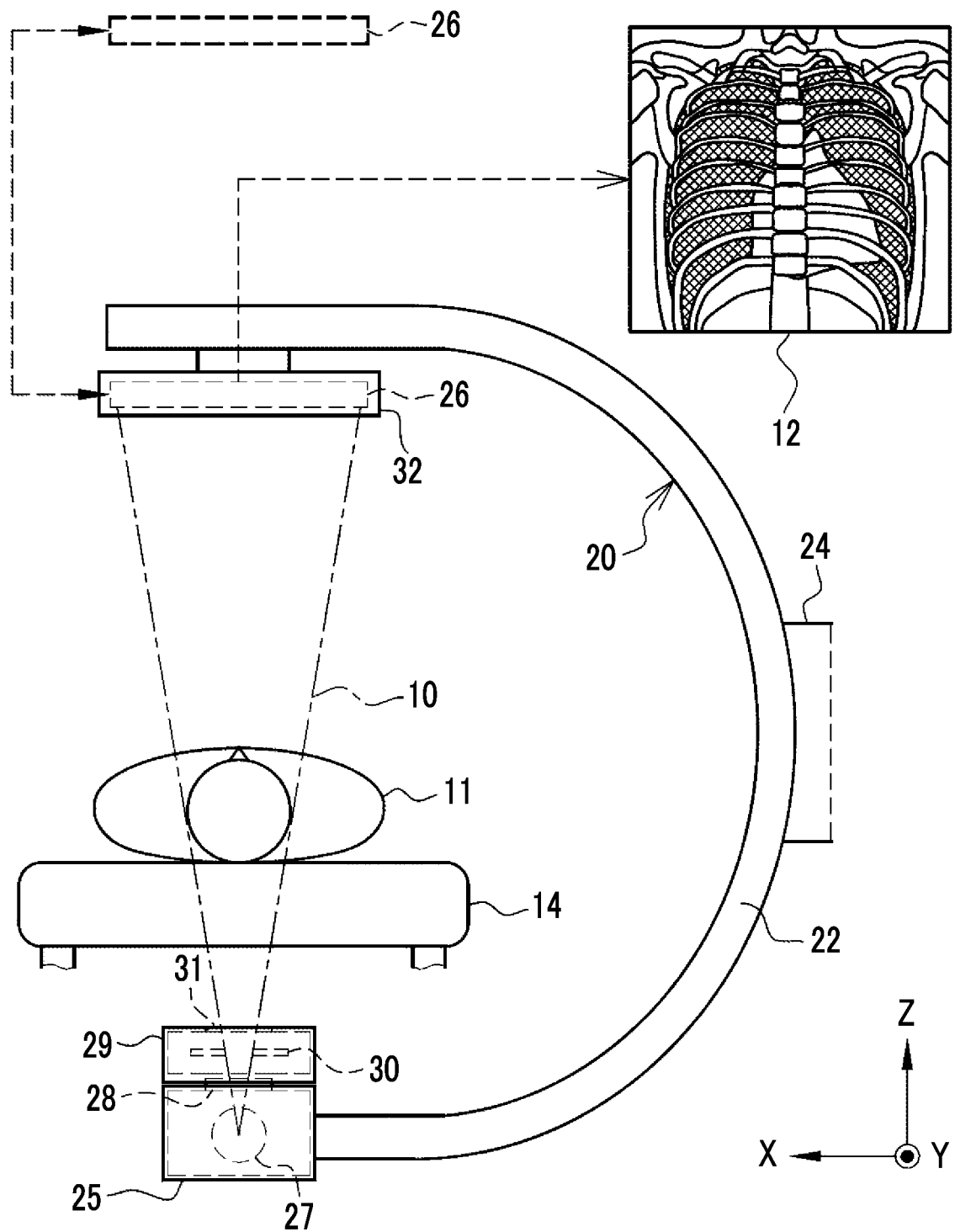
FIG. 2 is a diagram illustrating an arm portion and the like of the radiography apparatus.

In FIGS. 1 and 2, a radiography apparatus 2 irradiates a subject 11 with radiation 10, such as X-rays or y-rays, to capture a radiographic image 12 of the subject 11. The radiography apparatus 2 can perform still image capture for capturing one radiographic image 12 and moving image capture for capturing a plurality of radiographic images 12 at a predetermined frame interval FI (see FIG. 7). The moving image capture is also called fluoroscopy. FIGS. 1 and 2 illustrate an aspect in which a radiology technician 13 takes a moving image of the chest of the subject 11 lying supine on an operating table 14 in an operating room.

The radiography apparatus 2 includes an arm portion 20 and a main body portion 21. The arm portion 20 has an arm 22 that has a substantially C-shape in a side view. The main body portion 21 has a support 23 that extends in the Z direction (height direction). The arm 22 and the support 23 are connected through a connection portion 24. The connection portion 24 makes it possible for the arm 22 to be movable in the Z direction with respect to the support 23 and makes it possible to adjust the height according to the position of the subject 11. Further, the arm 22 is rotatable about a rotation axis that passes through the connection portion 24 and extends along the X direction orthogonal to the Z direction.

A radiation source 25 is attached to one end of the arm 22, and a radiation detector 26 is attached to the other end of the arm 22. In FIGS. 1 and 2, the radiation source 25 is located below the subject 11, and the radiation detector 26 is located above the subject 11. This positional relationship is called an undertube posture. Conversely, in a case in which the radiation source 25 is located above the subject 11 and the radiation detector 26 is located below the subject 11, this positional relationship is called an overtube posture. In the undertube posture, a portion of the radiation 10 from the radiation source 25 is shielded by the operating table 14. Therefore, it is possible to reduce unnecessary exposure to the radiology technician 13 or the like around the subject 11.

A radiation tube 27 that emits the radiation 10 is accommodated in the radiation source 25. The radiation source 25 is rotatable about a rotation axis along the X direction and about a rotation axis along the Y direction orthogonal to the X direction and the Z direction such that the irradiation angle of the radiation 10 with respect to the subject 11 can be adjusted.

The radiation source 25 is provided with a rectangular radiation transmission window 28 that transmits the radiation 10. The radiation 10 emitted from the radiation tube 27 is emitted from the radiation source 25 through the radiation transmission window 28.

An irradiation field limiter 29 is attached to the radiation transmission window 28. The irradiation field limiter 29 is also called a collimator and sets the irradiation field of the radiation 10. Specifically, the irradiation field limiter 29 has a plurality of shielding plates 30 that are made of, for example, lead and shield the radiation 10 transmitted through the radiation transmission window 28. Then, the shielding plates 30 are moved to change the size of, for example, a rectangular opening defined by the shielding plates 30, thereby setting the irradiation field of the radiation 10. An irradiation opening 31 is formed in a surface of the irradiation field limiter 29 which faces the radiation transmission window 28. The radiation 10 whose irradiation field has been set by the shielding plates 30 is emitted to the subject 11 through the irradiation opening 31.

The radiation detector 26 detects the radiation 10 transmitted through the subject 11 and outputs the radiographic image 12. The radiation detector 26 is accommodated in a holder 32 that is provided at the other end of the arm 22 so as to face the radiation source 25. The radiation detector 26 may be detached from the holder 32 and then used. That is, the radiation detector 26 is removable. In a case in which the radiation detector 26 is accommodated in the holder 32 and then used, it performs wired communication through, for example, a contact provided in the holder 32. On the other hand, in a case in which the radiation detector 26 is detached from the holder 32 and then used, the radiation detector 26 performs wireless communication. Therefore, the radiation detector 26 is provided with a battery (not illustrated).

A battery 40, a voltage generator 41, and an imaging control device 42 are provided in the main body portion 21. In addition, a display 43 and an operation input unit 44 are provided on a top surface of the main body portion 21.

The battery 40 stores power to be supplied to each unit of the radiography apparatus 2. The battery 40 can be detached from the main body portion 21 and then charged. In a case in which the radiation detector 26 is accommodated in the holder 32, a battery of the radiation detector 26 is charged by the battery 40. The voltage generator 41 generates a tube voltage to be applied to the radiation tube 27. The radiation tube 27 and the voltage generator 41 are connected by a voltage cable (not illustrated). The tube voltage generated by the voltage generator 41 is supplied to the radiation tube 27 through the voltage cable.

The imaging control device 42 controls radiography by the radiation source 25 and the radiation detector 26. In addition, the imaging control device 42 performs image processing on the radiographic image 12 output from the radiation detector 26. That is, the imaging control device 42 is an example of an "image processing device" according to the technology of the present disclosure.

The display 43 displays various screens. The various screens include, for example, an image display screen 125 (see FIGS. 15 and 16) for displaying the radiographic image 12. The operation input unit 44 receives the input of various operations by the radiology technician 13 through various screens displayed on the display 43.

Four wheels 45 are attached to a lower part of the main body portion 21 in the front, rear, left, and right directions. The main body portion 21 and thus the radiography apparatus 2 can be moved in the hospital by the wheels 45.

Figure 3:
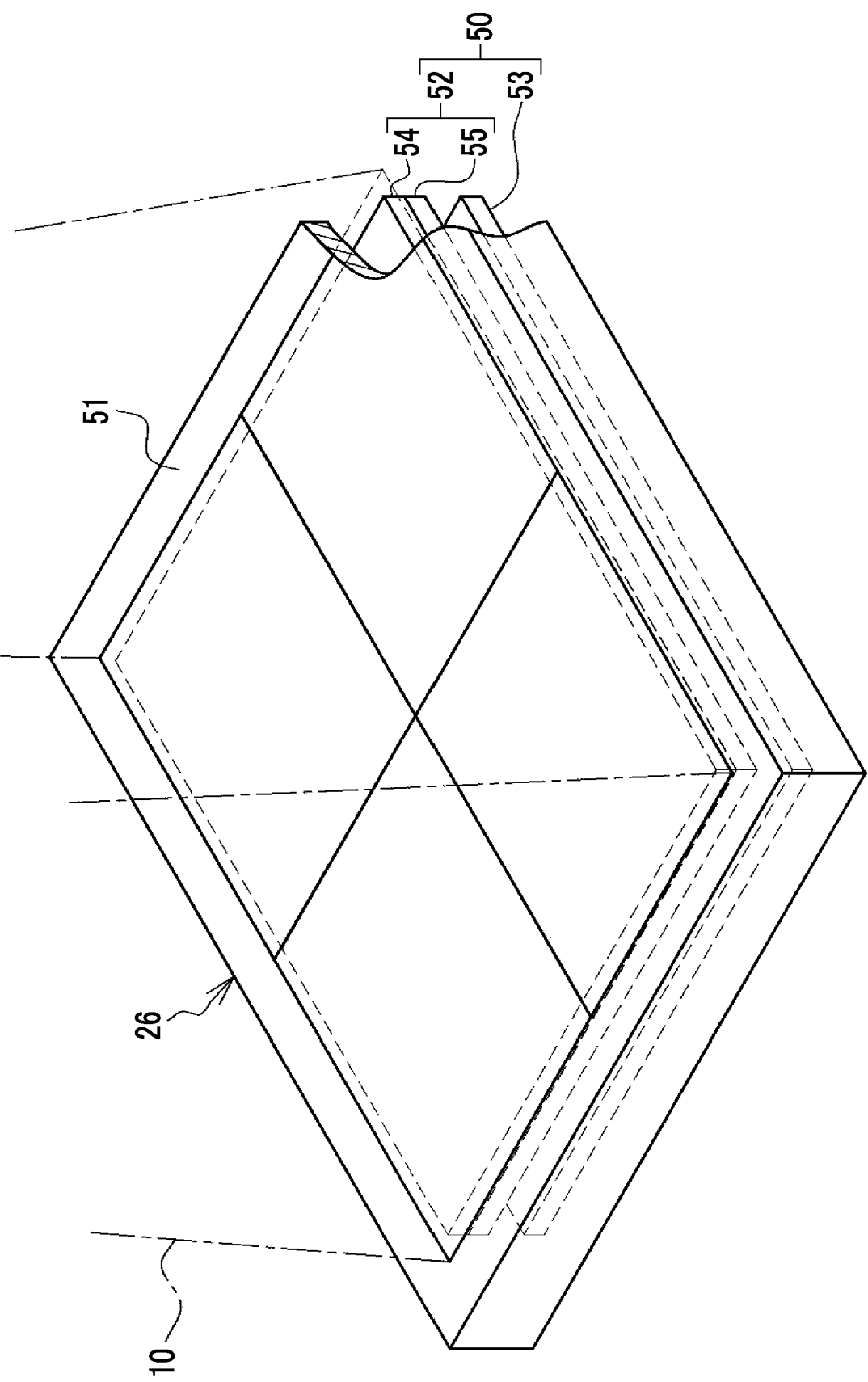
FIG. 3 is a perspective view illustrating a radiation detector.

In FIG. 3, the radiation detector 26 comprises an image output unit 50 that detects the radiation 10 transmitted through the subject 11 and outputs the radiographic image 12 represented by an electric signal and a portable housing 51 in which the image output unit 50 is provided. The image output unit 50 has a panel unit 52 and a circuit unit 53. The panel unit 52 includes a scintillator 54 and a light detection substrate 55. The radiation detector 26 is called a flat panel detector (FPD).

The scintillator 54 and the light detection substrate 55 are stacked in the order of the scintillator 54 and the light detection substrate 55 as viewed from the front side of the housing 51 on which the radiation 10 is incident. The scintillator 54 has a phosphor, such as CsI:Tl (thallium-activated cesium iodide) or GOS ($Gd_2O_2S$:Tb, terbium-activated gadolinium oxysulfide), converts the incident radiation 10 into visible light, and emits the visible light. The light detection substrate 55 detects the visible light emitted from the scintillator 54 and converts it into an electric signal. Specifically, the light detection substrate 55 has a plurality of pixels which are arranged in a two-dimensional matrix. As is well known, the pixel includes a photoelectric conversion unit that generates charge (electron-hole pair) using incident visible light and accumulates the charge and a switching element, such as a thin film transistor (TFT), that controls the accumulation of charge in the photoelectric conversion unit and the reading of charge from the photoelectric conversion unit.

The circuit unit 53 controls the driving of, for example, the switching elements in the light detection substrate 55. In addition, the circuit unit 53 generates a radiographic image on the basis of the electric signal output from the light detection substrate 55. Further, the scintillator 54 and the light detection substrate 55 may be stacked in the order of the light detection substrate 55 and the scintillator 54 as viewed from the front side. Furthermore, the radiation detector 26 may not be an indirect conversion type that converts the radiation 10 converted into visible light by the scintillator 54 into an electric signal as in this example, but may be a direct conversion type that directly converts the radiation 10 into an electric signal. Hereinafter, in some cases, the electric signal is referred to as a "pixel value".

Figure 4:
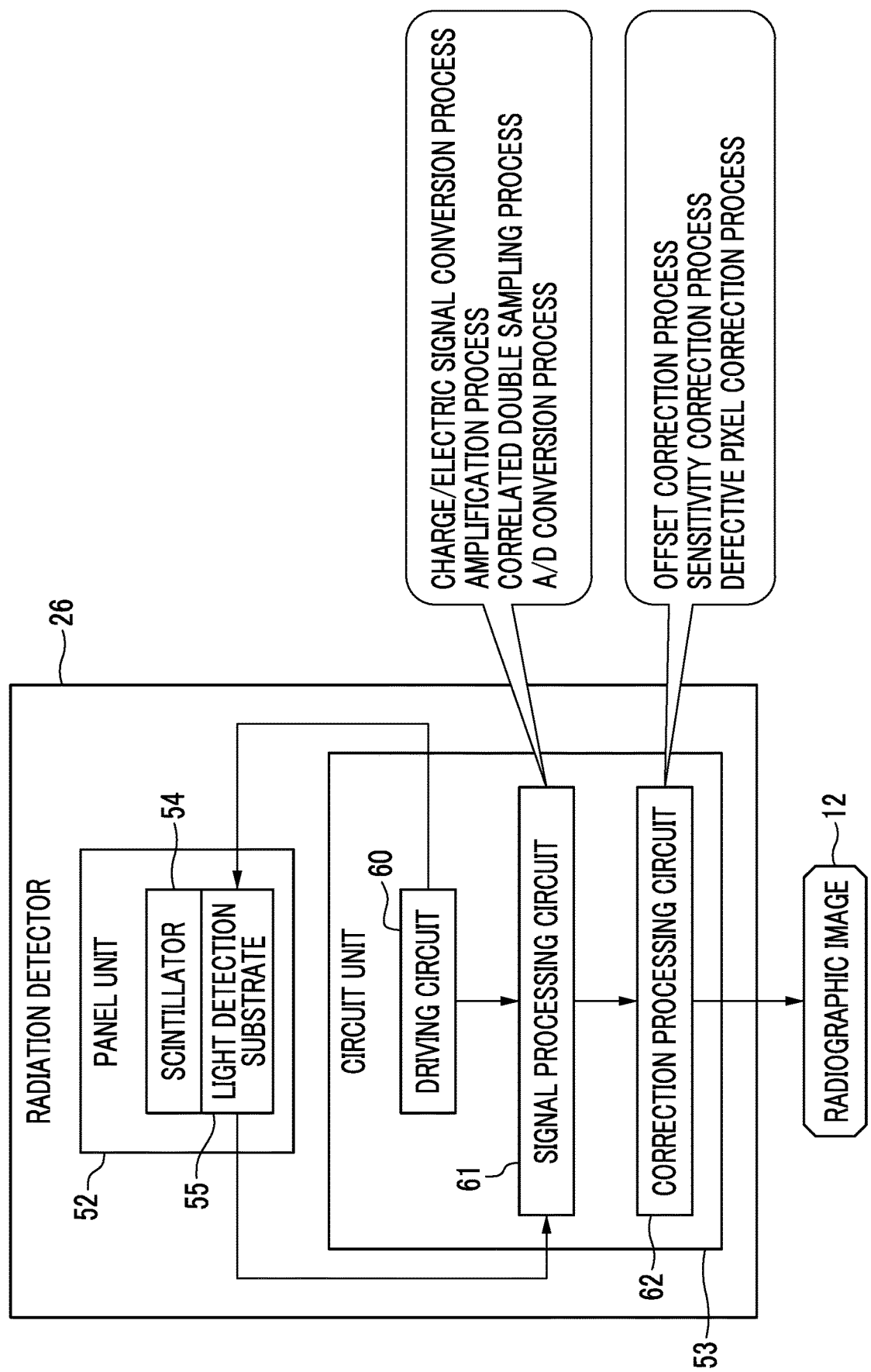
FIG. 4 is a block diagram illustrating the radiation detector.

In FIG. 4, the circuit unit 53 of the radiation detector 26 has a driving circuit 60, a signal processing circuit 61, and a correction processing circuit 62. The driving circuit 60 emits a gate pulse to each row of gate electrodes of the TFTs of each pixel in the light detection substrate 55. Therefore, a reset operation, an accumulation operation, and a reading operation are performed in the light detection substrate 55. The reset operation is an operation that reads dark charge from the photoelectric conversion unit to reset the photoelectric conversion unit. The accumulation operation is an operation that accumulates charge corresponding to the arrival dose of the radiation 10 in the photoelectric conversion unit. The reading operation is an operation that reads the charge accumulated in the photoelectric conversion unit to the signal processing circuit 61.

The signal processing circuit 61 has an integrating amplifier, a gain amplifier, a correlated double sampling (CDS) circuit, a multiplexer, and an analog-to-digital (A/D) converter (which are not illustrated).

The integrating amplifier performs a charge/electric signal conversion process that accumulates and integrates the charge input from the photoelectric conversion unit and outputs an analog electric signal corresponding to the accumulated charge. The integrating amplifier has an amplifier reset switch. The amplifier reset switch is turned on to discard the charge accumulated in the integrating amplifier. In the reset operation, no electric signal is output from the integrating amplifier and charge is discarded. In the reading operation, after an electric signal corresponding to the charge is output from the integrating amplifier, the amplifier reset switch is turned on to discard the charge.

The gain amplifier performs an amplification process that amplifies the electric signal output from the integrating amplifier with a predetermined gain value. The CDS circuit performs a well-known correlated double sampling process on the electric signal amplified by the gain amplifier to remove a reset noise component of the integrating amplifier from the electric signal. The integrating amplifier, the gain amplifier, and the CDS circuit are provided for each column of a plurality of pixels arranged in a two-dimensional matrix.

The multiplexer sequentially selects the CDS circuits in each column one by one and serially inputs the electric signals output from each CDS circuit to the A/D converter. The A/D converter performs an A/D conversion process on the input electric signal and outputs a digital electric signal. The digital electric signal output from the A/D converter is output as the radiographic image 12 to the correction processing circuit 62.

The correction processing circuit 62 performs an offset correction process, a sensitivity correction process, and a defective pixel correction process on the radiographic image 12 from the signal processing circuit 61. The offset correction process is a process that subtracts an offset correction image detected in a state in which the radiation 10 is not emitted from the radiographic image 12 in units of pixels. The correction processing circuit 62 performs the offset correction process to remove fixed pattern noise caused by, for example, dark charge from the radiographic image 12. The sensitivity correction process is a process that corrects, for example, a variation in the sensitivity of the photoelectric conversion unit in each pixel and a variation in the output characteristics of the signal processing circuit 61 on the basis of sensitivity correction data. The defective pixel correction process is a process that linearly interpolates the value of a defective pixel with the values of surrounding normal pixels on the basis of the information of the defective pixel having an abnormal value, which is generated during shipping or a regular inspection. The offset correction process, the sensitivity correction process, and the defective pixel correction process are essential processes in order to make the quality of the radiographic image 12 suitable for observation. The radiographic image 12 subjected to the various processes is finally output from the radiation detector 26.

Figure 5:
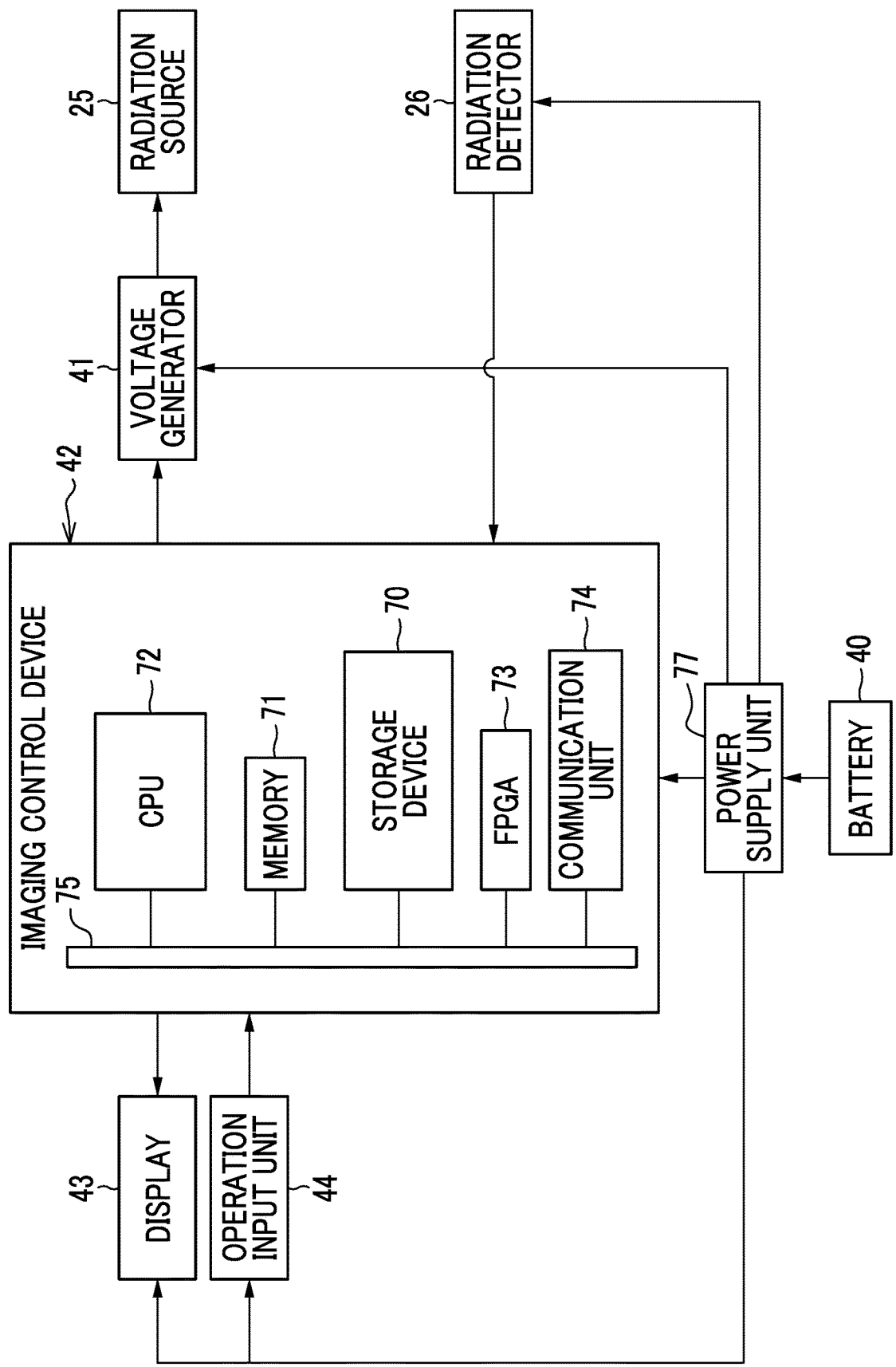
FIG. 5 is a block diagram illustrating a computer forming an imaging control device.

In FIG. 5, the computer forming the imaging control device 42 comprises a storage device 70, a memory 71, a central processing unit (CPU) 72, a field programmable gate array (FPGA) 73, and a communication unit 74. These are connected to each other through a bus line 75.

The storage device 70 is, for example, a hard disk drive that is provided in the computer forming the imaging control device 42. The storage device 70 stores, for example, a control program, such as an operating system, various application programs, and various kinds of data associated with these programs. A solid state drive may be used instead of the hard disk drive.

The memory 71 is a work memory that is used by the CPU 72 to perform processes. The CPU 72 loads the program stored in the storage device 70 to the memory 71 and performs a process corresponding to the program to control the overall operation of each unit of the computer. The CPU 72 is an example of a "processor" according to the technology of the present disclosure.

The FPGA 73 is a type of programmable logic device (PLD) in which the circuit configuration of a logic circuit can be changed after manufacturing. The FPGA 73 mainly performs image processing on the radiographic image 12 from the radiation detector 26. The communication unit 74 communicates various kinds of data with, for example, the radiation detector 26 and the voltage generator 41. A dedicated electric circuit having a dedicated circuit configuration designed to perform a specific process, such as an application specific integrated circuit (ASIC), may be used instead of the FPGA 73.

A power supply unit 77 is connected to the battery 40. The power supply unit 77 supplies power from the battery 40 to each unit of the radiography apparatus 2 including the radiation detector 26. Specifically, the power supply unit 77 includes, for example, a direct current (DC)-DC converter that converts a DC voltage from the battery 40 into a voltage having a value corresponding to a supply destination and a voltage stabilization circuit that stabilizes the value of the converted voltage.

Figure 6:
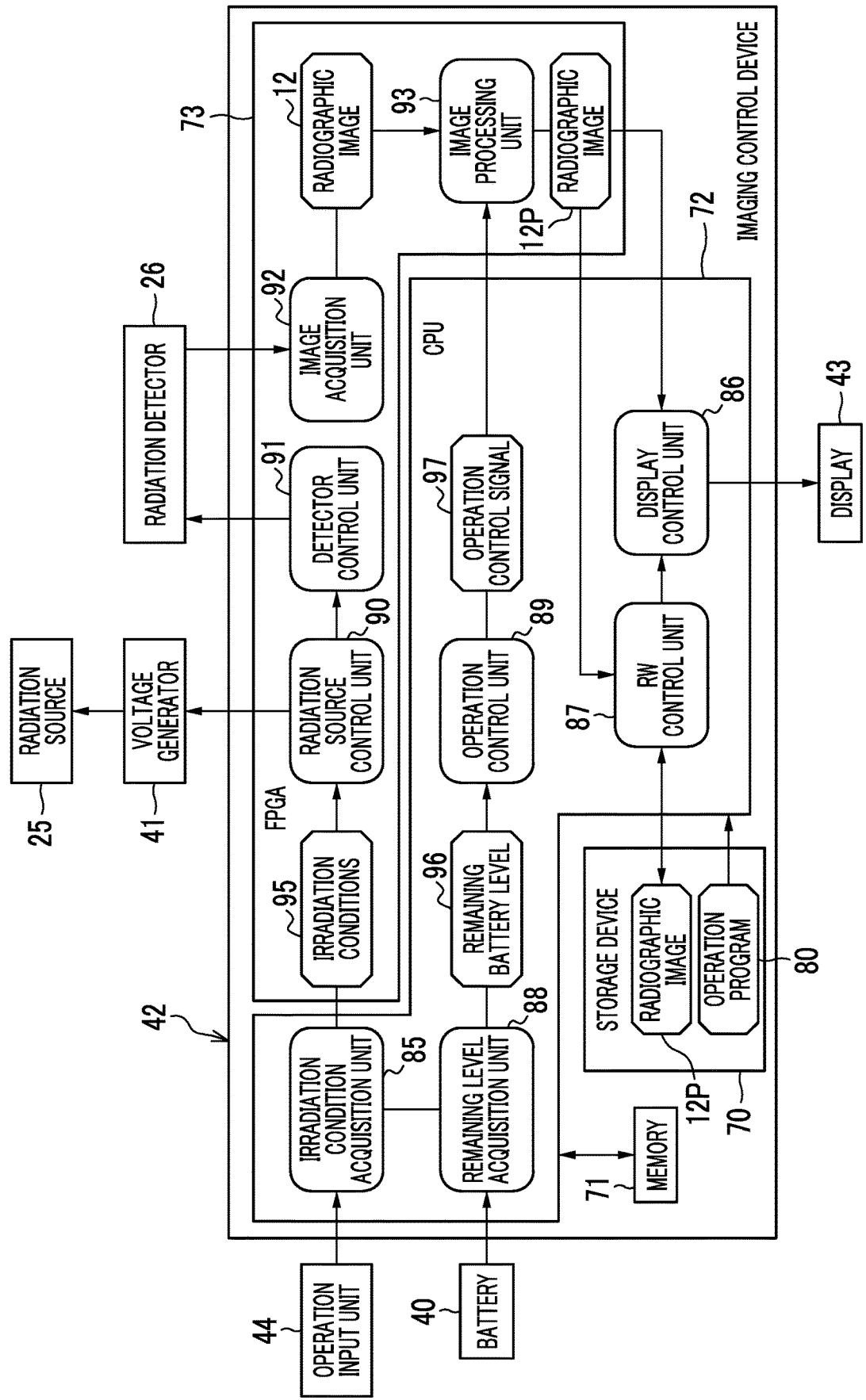
FIG. 6 is a block diagram illustrating the imaging control device.

In FIG. 6, an operation program 80 is stored in the storage device 70 of the imaging control device 42. The operation program 80 is an application program for causing the computer to function as the imaging control device 42. That is, the operation program 80 is an example of an "operation program for a radiography apparatus" according to the technology of the present disclosure.

In a case in which the operation program 80 is started, the CPU 72 of the imaging control device 42 functions as an irradiation condition acquisition unit 85, a display control unit 86, a read and write (hereinafter, abbreviated to RW) control unit 87, a remaining level acquisition unit 88, and an operation control unit 89 in cooperation with, for example, the memory 71. In addition, the FPGA 73 functions as a radiation source control unit 90, a detector control unit 91, an image acquisition unit 92, and an image processing unit 93.

The irradiation condition acquisition unit 85 acquires irradiation conditions 95 of the radiation 10 input by the radiology technician 13 through the operation input unit 44. The irradiation condition acquisition unit 85 outputs the irradiation conditions 95 to the radiation source control unit 90.

Figure 7:
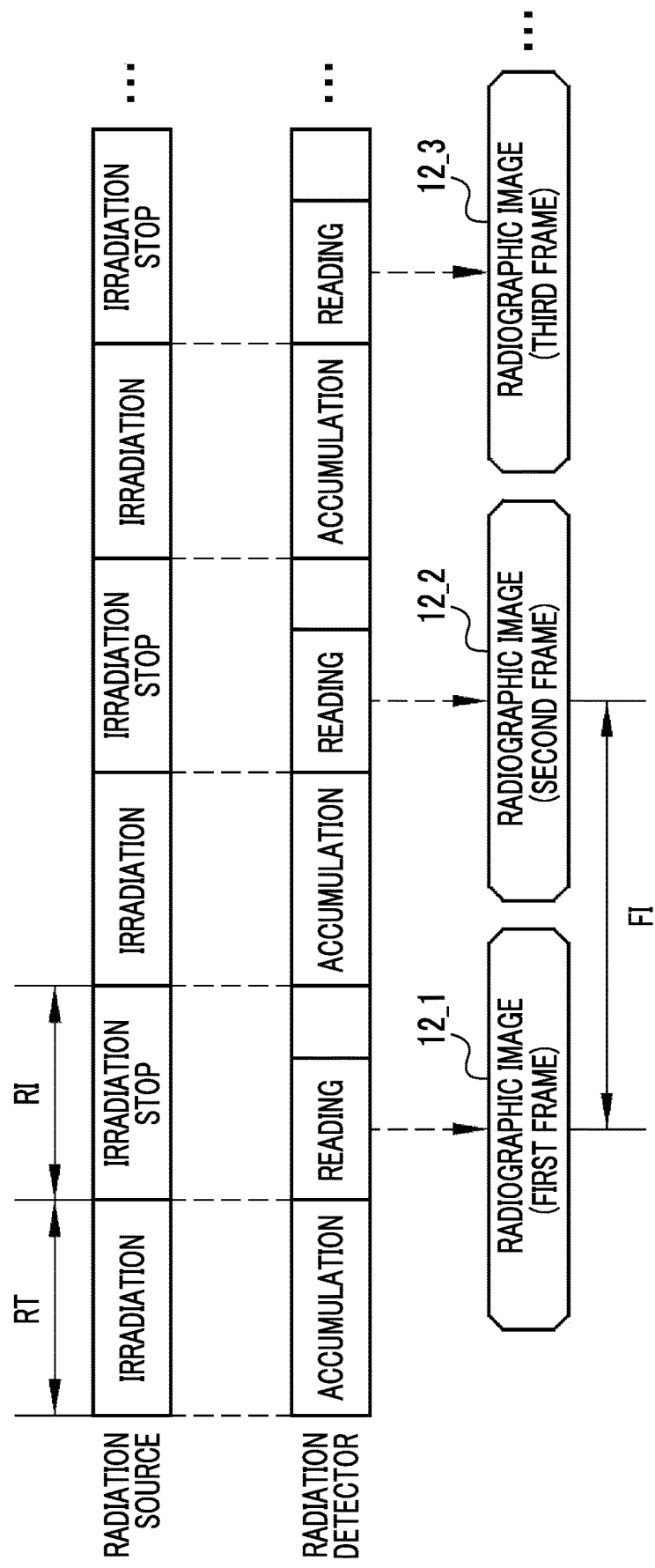
FIG. 7 is a diagram illustrating the operation timing of a radiation source and the radiation detector in the capture of a moving image.

The irradiation conditions 95 in the case of still image capture include a tube voltage applied to the radiation tube 27, a tube current, and an irradiation time RT of the radiation 10 (see FIG. 7). The irradiation conditions 95 in the case of moving image capture include an irradiation interval RI (see FIG. 7) of the radiation 10 in addition to the tube voltage, the tube current, and the irradiation time RT. In the case of the moving image capture, the irradiation conditions 95 are set such that the dose of the radiation 10 is less than that in the case of the still image capture. In addition, instead of the tube current and the irradiation time RT, a tube current irradiation time product may be used as the irradiation condition 95.

The radiation source control unit 90 controls the operation of the radiation source 25. The radiation source control unit 90 sets the irradiation conditions 95 from the irradiation condition acquisition unit 85 in the voltage generator 41. In a case in which the radiology technician 13 inputs a radiography start command through an irradiation switch (not illustrated), the radiation source control unit 90 directs the radiation tube 27 to generate the radiation 10 under the set irradiation conditions 95. The radiation source control unit 90 outputs, to the detector control unit 91, an irradiation start notification signal notifying the start of the emission of the radiation 10 and an irradiation end notification signal notifying the end of the emission of the radiation 10.

The detector control unit 91 controls the operation of the radiation detector 26. The detector control unit 91 directs the radiation detector 26 to perform the accumulation operation in accordance with the irradiation start notification signal from the radiation source control unit 90. Further, the detector control unit 91 directs the radiation detector 26 to perform the reading operation in accordance with the irradiation end notification signal from the radiation source control unit 90. Then, the detector control unit 91 directs the radiation detector 26 to output the radiographic image 12. In addition, the radiation detector 26 may have the function of detecting the start and end of the emission of the radiation 10. The radiation detector 26 may determine the timing of the accumulation operation and the reading operation. In this case, the detector control unit 91 is not necessary.

The image acquisition unit 92 acquires the radiographic image 12 output from the radiation detector 26. The image acquisition unit 92 outputs the radiographic image 12 from the radiation detector 26 to the image processing unit 93 at a frame interval FI. In addition, the interval at which the image acquisition unit 92 outputs the radiographic image 12 to the image processing unit 93 is not limited to the frame interval FI. For example, odd-numbered frames may be thinned out and the radiographic image 12 may be output to the image processing unit 93 at a frame interval 2FI.

The display control unit 86 performs control to display various screens on the display 43. For example, the display control unit 86 generates an image display screen 125 for displaying a radiographic image 12P which has been subjected to the image processing and output from the image processing unit 93 and displays the image display screen 125 on the display 43. In the following description, the radiographic image 12P subjected to the image processing is also referred to as the radiographic image 12 in a case in which it does not need to be particularly distinguished.

The RW control unit 87 controls the reading of various kinds of data from the storage device 70 and the storage of various kinds of data in the storage device 70. For example, the RW control unit 87 stores the radiographic image 12P which has been subjected to the image processing and output from the image processing unit 93 in the storage device 70. Further, the RW control unit 87 reads the radiographic image 12P subjected to the image processing from the storage device 70 and outputs the radiographic image 12P to the display control unit 86.

The remaining level acquisition unit 88 acquires a remaining level 96 of the battery 40 (hereinafter, abbreviated to a remaining battery level) at a predetermined time interval. The remaining level acquisition unit 88 outputs the remaining battery level 96 to the operation control unit 89. The remaining level acquisition unit 88 is an example of an "acquisition unit" according to the technology of the present disclosure.

The operation control unit 89 generates an operation control signal 97 corresponding to the remaining battery level 96 and outputs the operation control signal 97 to the image processing unit 93. The operation control unit 89 controls the operation of the image processing unit 93 using the operation control signal 97.

As illustrated in FIG. 7, in the moving image capture, the radiation source 25 emits the radiation 10 at the tube voltage, the tube current, the irradiation time RT, and the irradiation interval RI set as the irradiation conditions 95. That is, the radiation 10 is intermittently emitted a plurality of times at the predetermined irradiation interval RI. In the radiation detector 26, the accumulation operation is performed while the radiation 10 is being emitted (for the irradiation time RT). Then, the reading operation is performed at the timing when the emission of the radiation 10 ends. Therefore, a radiographic image 12_1 of a first frame, a radiographic image 12_2 of a second frame, a radiographic image 12_3 of a third frame, . . . are output at the predetermined frame interval FI. The frame interval FI is, for example, about 0.03 seconds (a frame rate of 30 frames/second). In the radiation detector 26, the reset operation is performed before the accumulation operation to remove unnecessary dark charge from the photoelectric conversion unit, which is not illustrated. In addition, an aspect may be adopted in which the radiation 10 is not intermittently emitted, but is continuously emitted, and the radiation detector 26 repeatedly performs the accumulation operation and the reading operation while the radiation 10 is continuously emitted.

Figure 8:
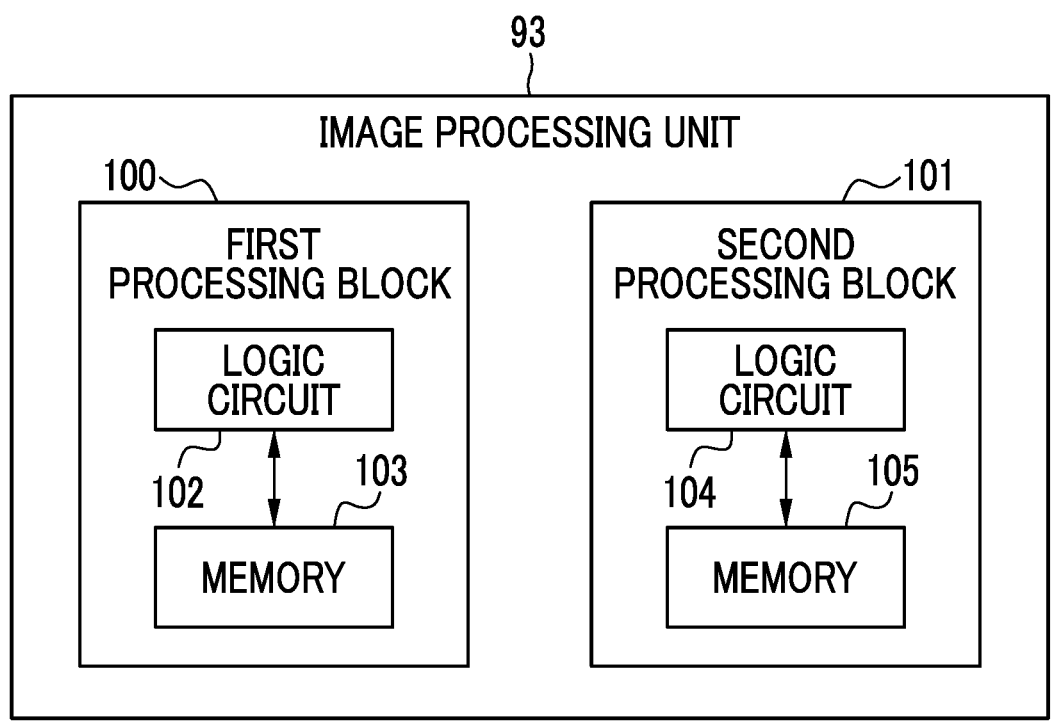
FIG. 8 is a block diagram illustrating an image processing unit.

In FIG. 8, the image processing unit 93 has a first processing block 100 and a second processing block 101. The first processing block 100 includes a logic circuit 102 and a memory 103. Similarly, the second processing block 101 includes a logic circuit 104 and a memory 105.

The logic circuits 102 and 104 include, for example, an AND circuit, an OR circuit, a NOT circuit, an exclusive OR circuit, a flip-flop, and a counter and perform image processing on the radiographic image 12. The memories 103 and 105 are memories that requires a refresh to replenish the charge accumulated in memory cells and are, for example, dynamic random access memories (DRAMs). The memories 103 and 105 are work memories that temporarily store intermediate data generated by processing.

Figure 9:
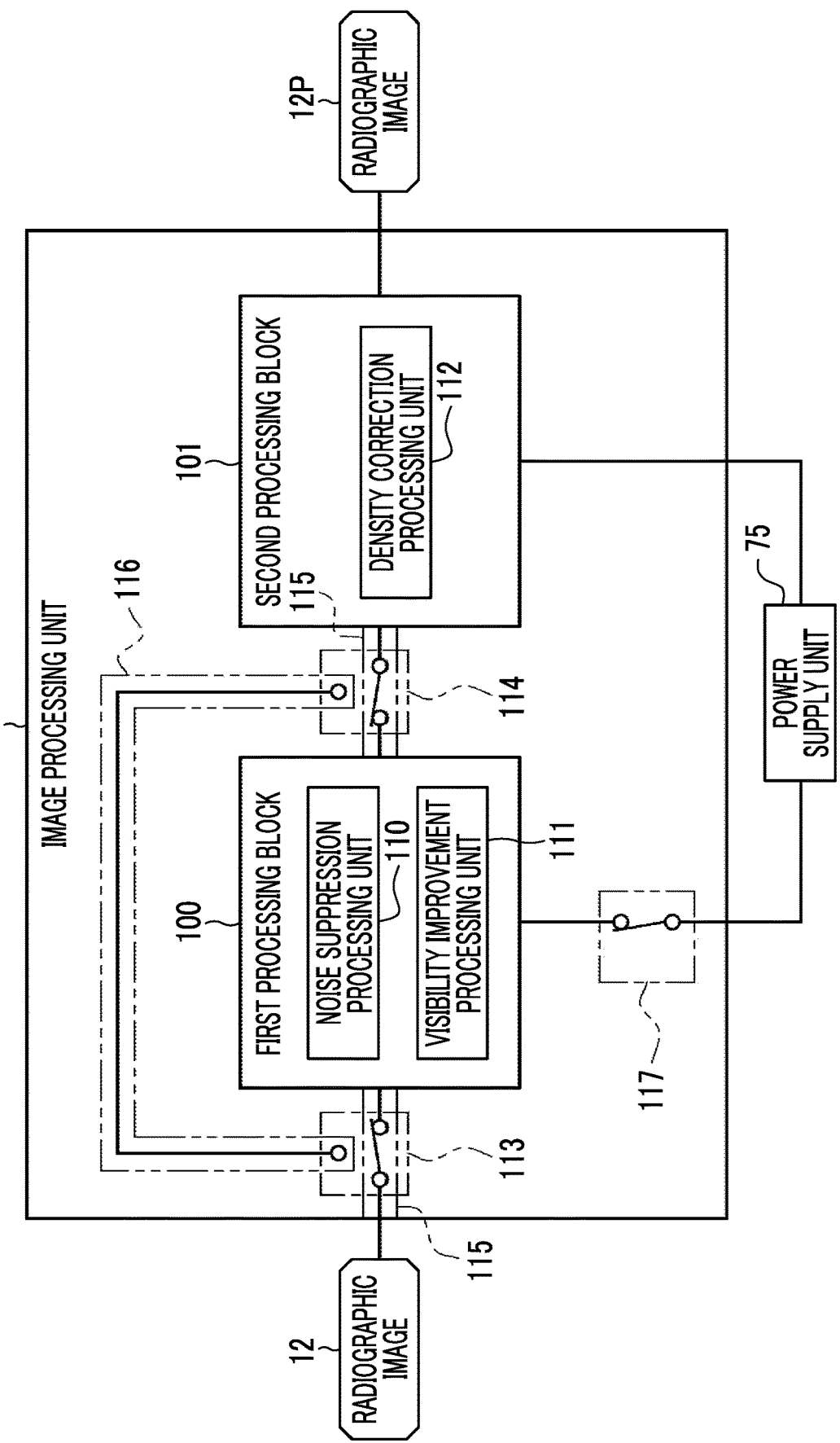
FIG. 9 is a diagram illustrating an operation aspect of the image processing unit in a case in which a remaining battery level is equal to or greater than a threshold value.
Figure 10:
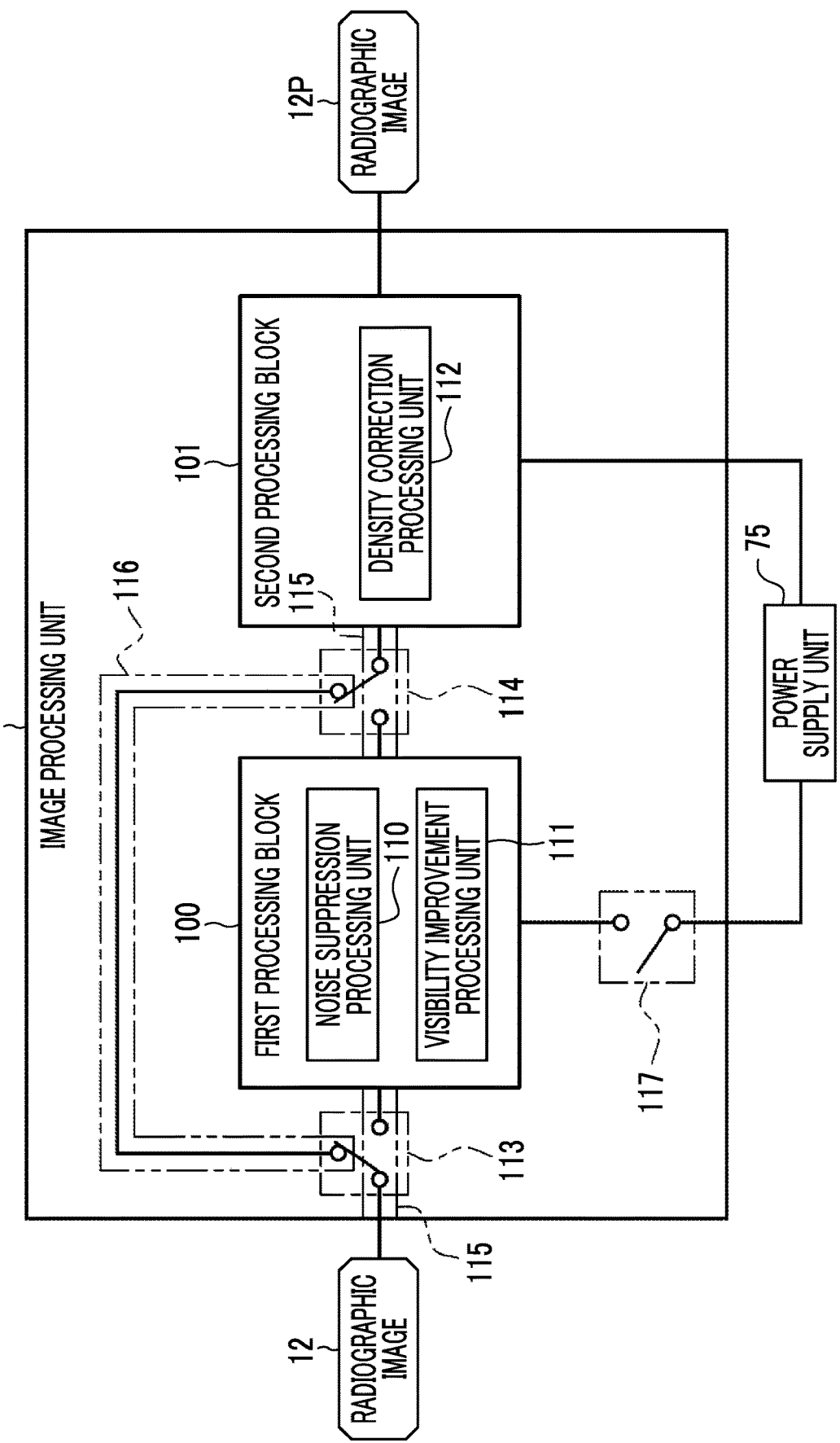
FIG. 10 is a diagram illustrating an operation aspect of the image processing unit in a case in which the remaining battery level is less than the threshold value.

As illustrated in FIGS. 9 and 10, the first processing block 100 functions as a noise suppression processing unit 110 and a visibility improvement processing unit 111. In addition, the second processing block 101 functions as a density correction processing unit 112.

A first switch 113 is provided in a stage in front of the first processing block 100. Further, a second switch 114 is provided in a stage that is behind the first processing block 100 and is in front of the second processing block 101, that is, between the first processing block 100 and the second processing block 101.

The first switch 113 and the second switch 114 operate in operative association with each other in response to the operation control signal 97 from the operation control unit 89. Specifically, the first switch 113 and the second switch 114 selectively switch between two paths of a first path 115 and a second path 116 in response to the operation control signal 97. The first path 115 is a path from the radiation detector 26 to the second processing block 101 through the first processing block 100. The second path 116 is a path from the radiation detector 26 to the second processing block 101 without passing through the first processing block 100.

A third switch 117 is provided between the power supply unit 77 and the first processing block 100. The third switch 117 is operated in response to the operation control signal 97 from the operation control unit 89. Specifically, the third switch 117 switches between a power supply state and a power supply stop state in response to the operation control signal 97. The power supply state is a state in which the power supply unit 77 and the first processing block 100 are connected and power is supplied from the power supply unit 77 to the first processing block 100. The power supply stop state is a state in which the power supply unit 77 and the first processing block 100 are disconnected and the supply of power from the power supply unit 77 to the first processing block 100 is stopped.

FIG. 9 illustrates a case in which the first path 115 is selected by the first switch 113 and the second switch 114 and the power supply state is selected by the third switch 117. In this case, a noise suppression process of the noise suppression processing unit 110 and a visibility improvement process of the visibility improvement processing unit 111 in the first processing block 100 and a density correction process of the density correction processing unit 112 in the second processing block 101 are performed on the radiographic image 12.

FIG. 10 illustrates a case in which the second path 116 is selected by the first switch 113 and the second switch 114 and the power supply stop state is selected by the third switch 117. In this case, the noise suppression process of the noise suppression processing unit 110 and the visibility improvement process of the visibility improvement processing unit 111 in the first processing block 100 are not performed on the radiographic image 12, and only the density correction process of the density correction processing unit 112 in the second processing block 101 is performed on the radiographic image 12.

The noise suppression process of the noise suppression processing unit 110 is performed as follows. That is, a spatial filter and a temporal filter (recursive filter) are applied to the radiographic image 12 from the radiation detector 26. In this way, a pixel value indicating a structure in the subject 11 and a pixel value based on noise are distinguished from each other. Then, the pixel value based on noise is removed from the radiographic image 12. The visibility improvement process of the visibility improvement processing unit 111 is a process of improving the visibility of the radiographic image 12. For example, the visibility improvement process is a process of applying a highlighting filter to the radiographic image 12 subjected to the noise suppression process to highlight the structure in the subject 11. The noise suppression process and the visibility improvement process are examples of "first image processing" according to the technology of the present disclosure. In addition, examples of the structure in the subject 11 include bones, organs, and blood vessels.

Figure 11:
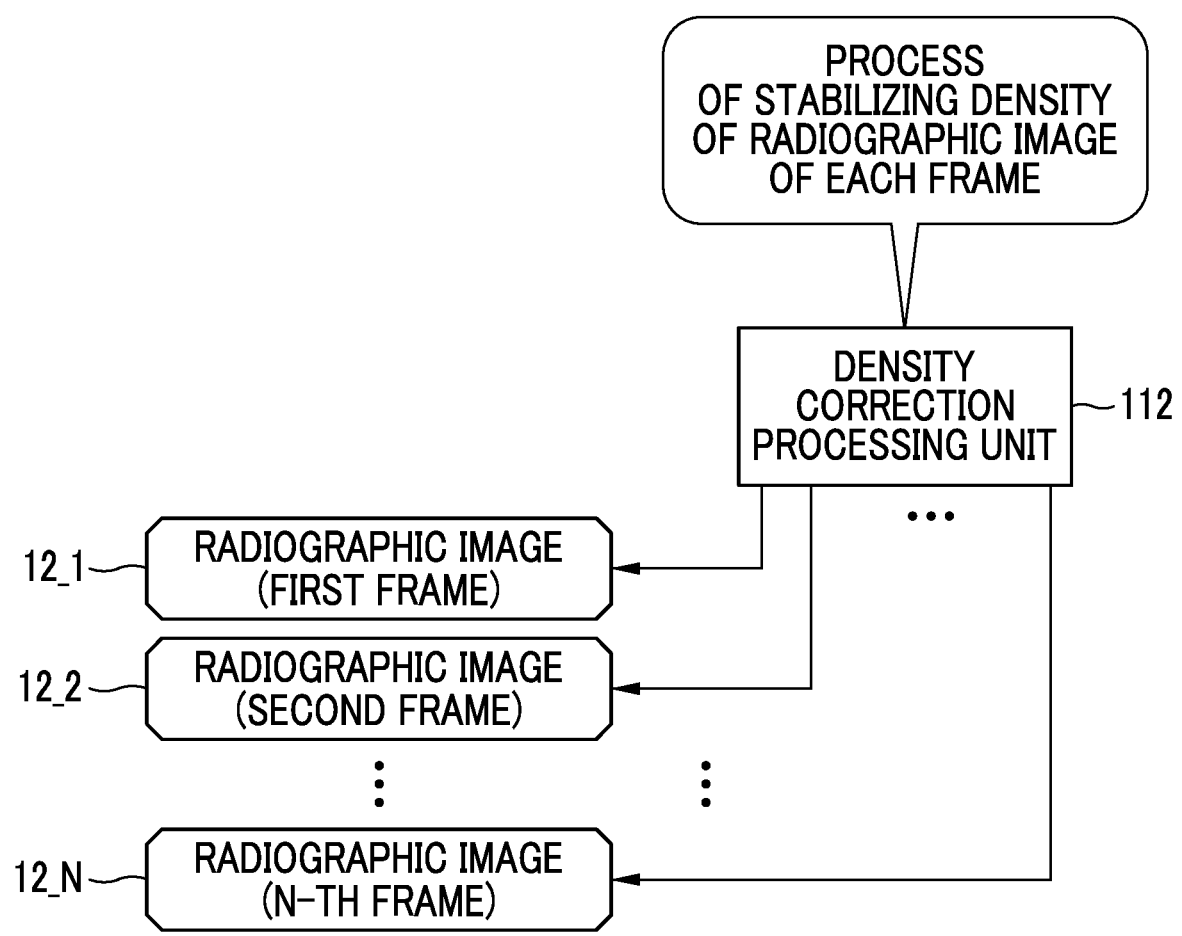
FIG. 11 is a diagram illustrating an outline of a density correction process of a density correction processing unit.

As illustrated in FIG. 11, the density correction process of the density correction processing unit 112 is a process of stabilizing the densities of the radiographic image 12_1 of the first frame, the radiographic image 12_2 of the second frame, . . . , the radiographic image 12_N of an N-th frame (N is the total number of frames) obtained by capturing a moving image of the same subject 11. The radiographic image 12_1 of the first frame, the radiographic image 12_2 of the second frame, . . . , the radiographic image 12_N of the N-th frame are examples of "two or more radiographic images of the same subject which have a time difference therebetween" according to the technology of the present disclosure.

Figure 12:
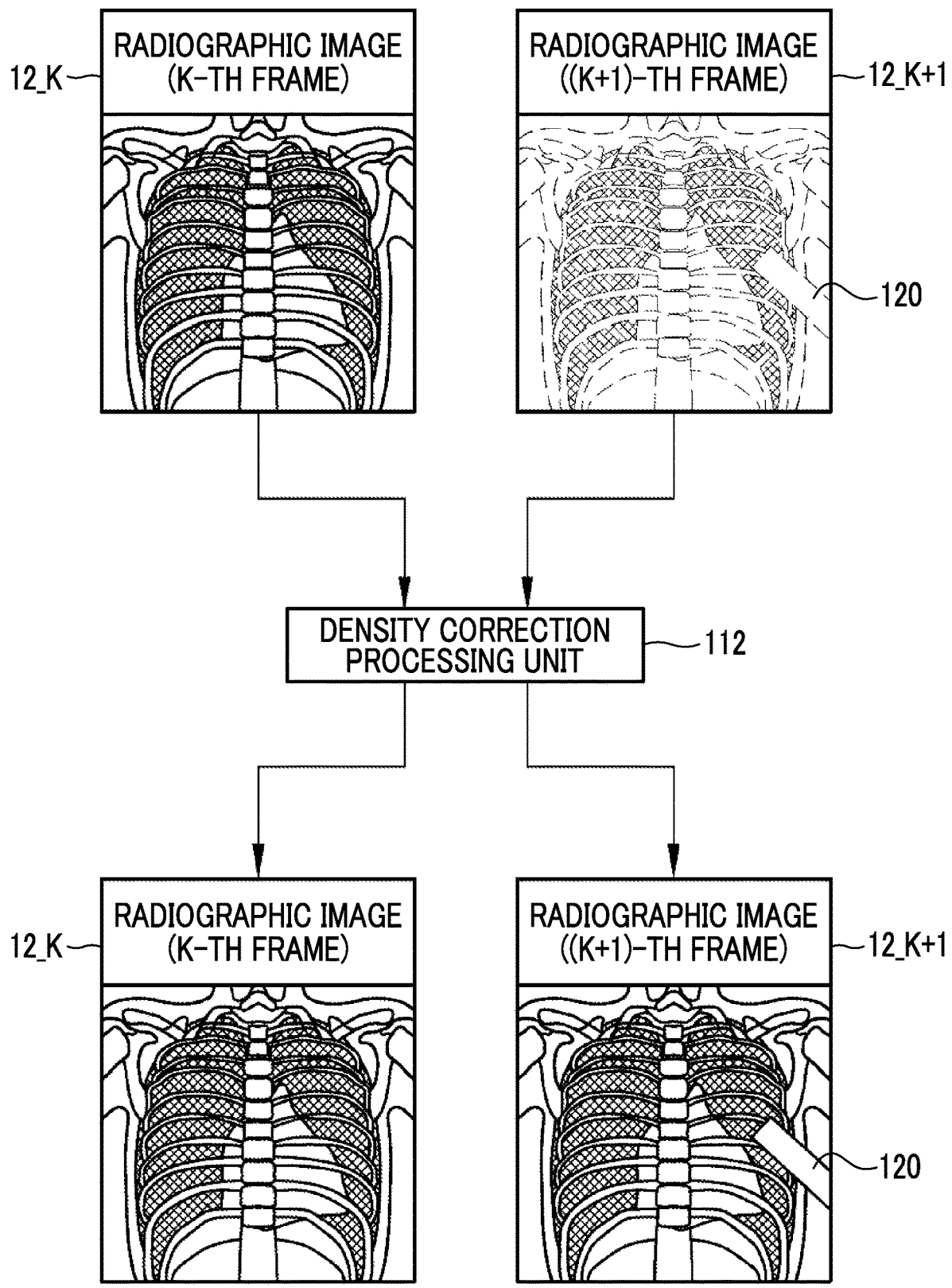
FIG. 12 is a diagram illustrating a specific example of the density correction process of the density correction processing unit.

For example, a case is considered in which the densities of a radiographic image 12_K of a K-th frame (K=1, 2, . . . , N−1) and a radiographic image 12_K+1 of a (K+1)-th frame are stabilized as illustrated in FIG. 12. The radiographic image 12_K of the K-th frame includes only the chest of the subject 11. On the other hand, the radiographic image 12_K+1 of the (K+1)-th frame includes a treatment tool 120 for surgery in addition to the chest of the subject 11. The treatment tool 120 is a metal tool, such as a bone cutting drill, a silicon or cement injection tool, a fracture fixation screw and bolt, or an artificial joint.

A density histogram of the radiographic image 12_K+1 of the (K+1)-th frame is significantly different from that of the radiographic image 12_K of the K-th frame since the treatment tool 120 is included. Therefore, in this state, the allocation of the gradation of a pixel value corresponding to the density histogram is also significantly different and there is a large difference in the density of the structure in the subject 11 between the radiographic image 12_K of the K-th frame and the radiographic image 12_K+1 of the (K+1)-th frame. As such, in a case in which there is a difference in density between the radiographic images 12 of each frame and the radiographic images 12 of each frame are displayed as a moving image, the difference in density appears as flicker that cannot be overlooked. Therefore, the density correction processing unit 112 adjusts the allocation of the gradation of the pixel values of the radiographic image 12_K of the K-th frame and the radiographic image 12_K+1 of the (K+1)-th frame such that the density of the structure of the subject 11 included in the radiographic image 12_K and the density of the structure of the subject 11 included in the radiographic image 12_K+1 are predetermined densities. The density correction process is an example of "second image processing" according to the technology of the present disclosure.

The noise suppression process of the noise suppression processing unit 110 and the visibility improvement process of the visibility improvement processing unit 111 may be performed as much as possible. However, even in a case in which these processes are not performed, there is no concern that the radiographic image 12 which is not suitable for observation will be generated. In contrast, in a case in which the density correction process of the density correction processing unit 112 is not performed, the radiographic image 12 that is not suitable for observation is generated. Therefore, the density correction process is a process that needs to be certainly performed in order to secure the radiographic image 12 that is suitable for observation.

Figure 13:
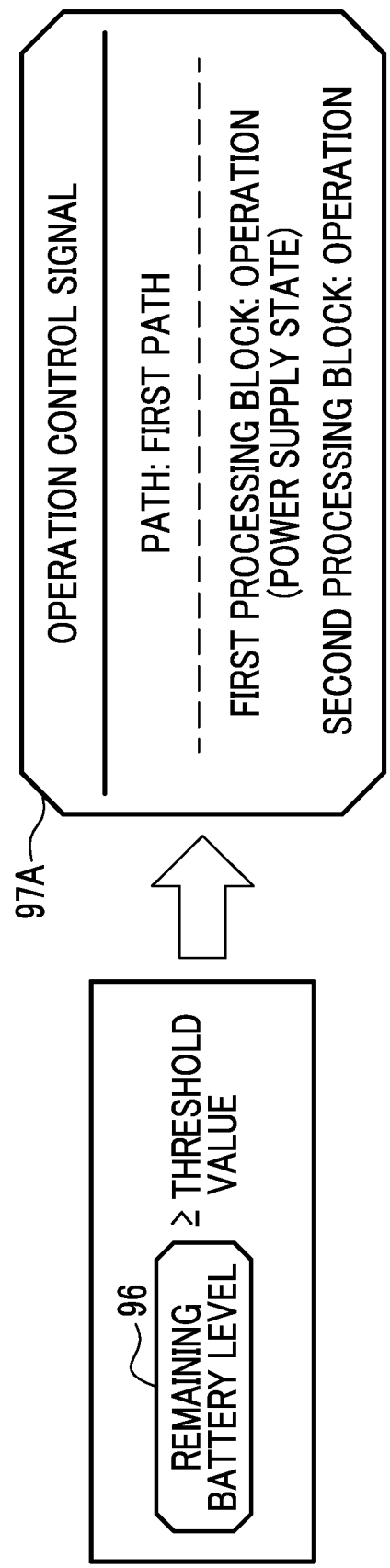
FIG. 13 is a diagram illustrating an operation control signal in a case in which the remaining battery level is equal to or greater than the threshold value.

As illustrated in FIG. 13, the content of an operation control signal 97A in a case in which the remaining battery level 96 is equal to or greater than a predetermined threshold value is that the first path 115 is selected by the first switch 113 and the second switch 114, the power supply state is selected by the third switch 117, and both the first processing block 100 and the second processing block 101 are operated. In the case of the operation control signal 97A, the image processing unit 93 operates in the state illustrated in FIG. 9.

Figure 14:
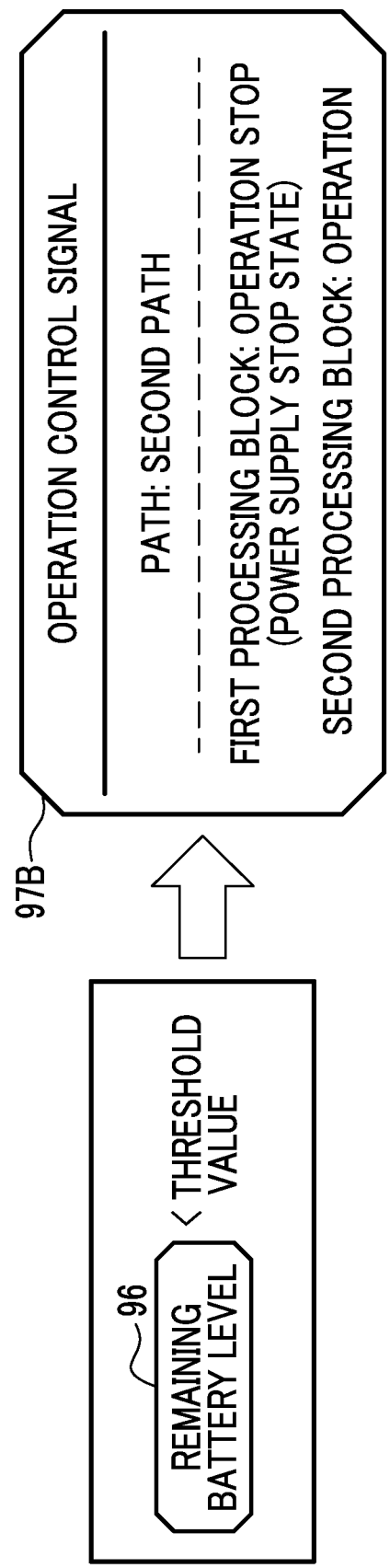
FIG. 14 is a diagram illustrating an operation control signal in a case in which the remaining battery level is less than the threshold value.

In contrast, as illustrated in FIG. 14, the content of an operation control signal 97B in a case in which the remaining battery level 96 is less than the threshold value is that the second path 116 is selected by the first switch 113 and the second switch 114, the power supply stop state is selected by the third switch 117, the operation of the first processing block 100 is stopped, and only the second processing block 101 is operated. In the case of the operation control signal 97B, the image processing unit 93 operates in the state illustrated in FIG. 10.

Figure 15:
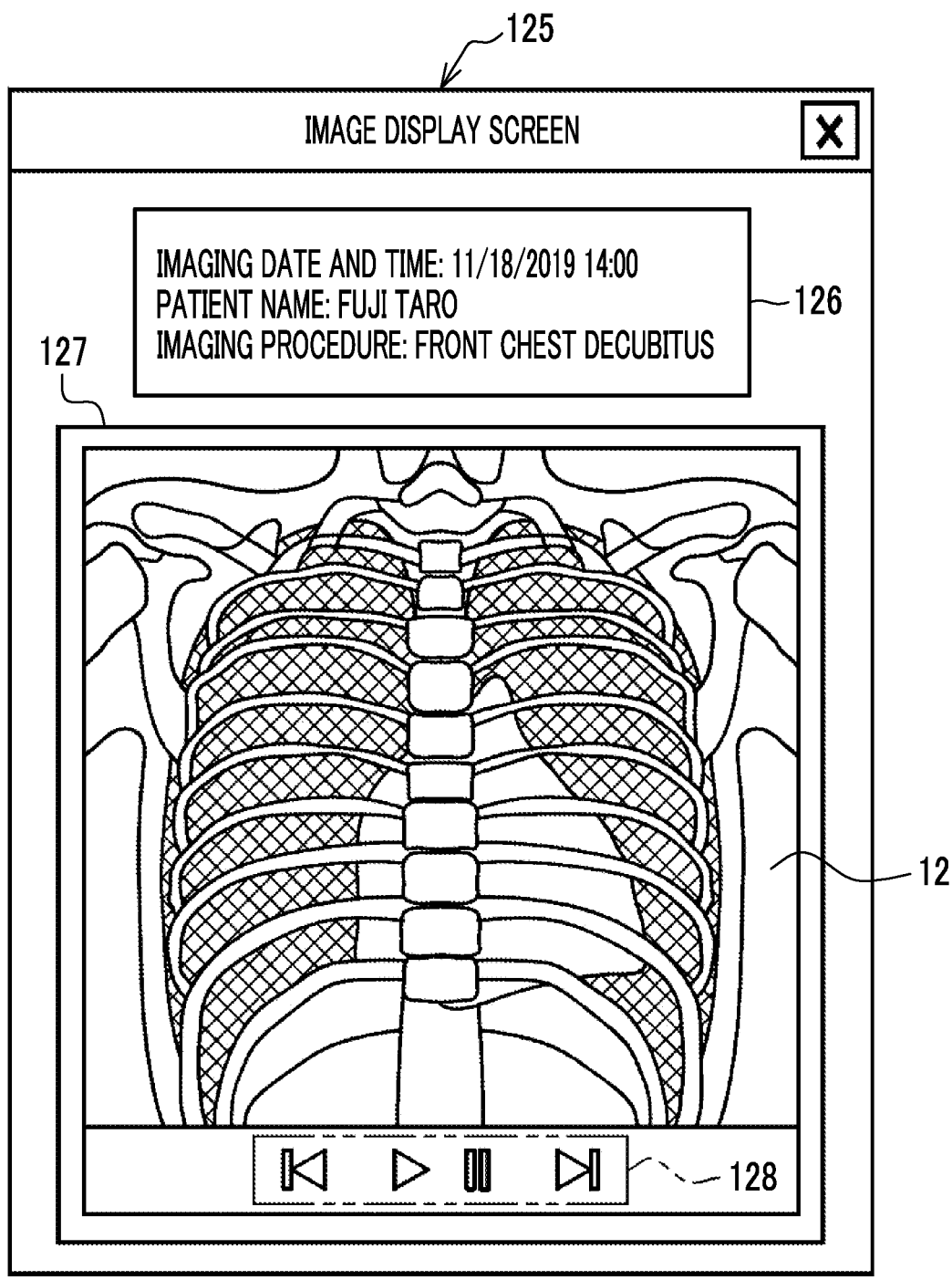
FIG. 15 is a diagram illustrating an image display screen in a case in which the remaining battery level is equal to or greater than the threshold value.
Figure 16:
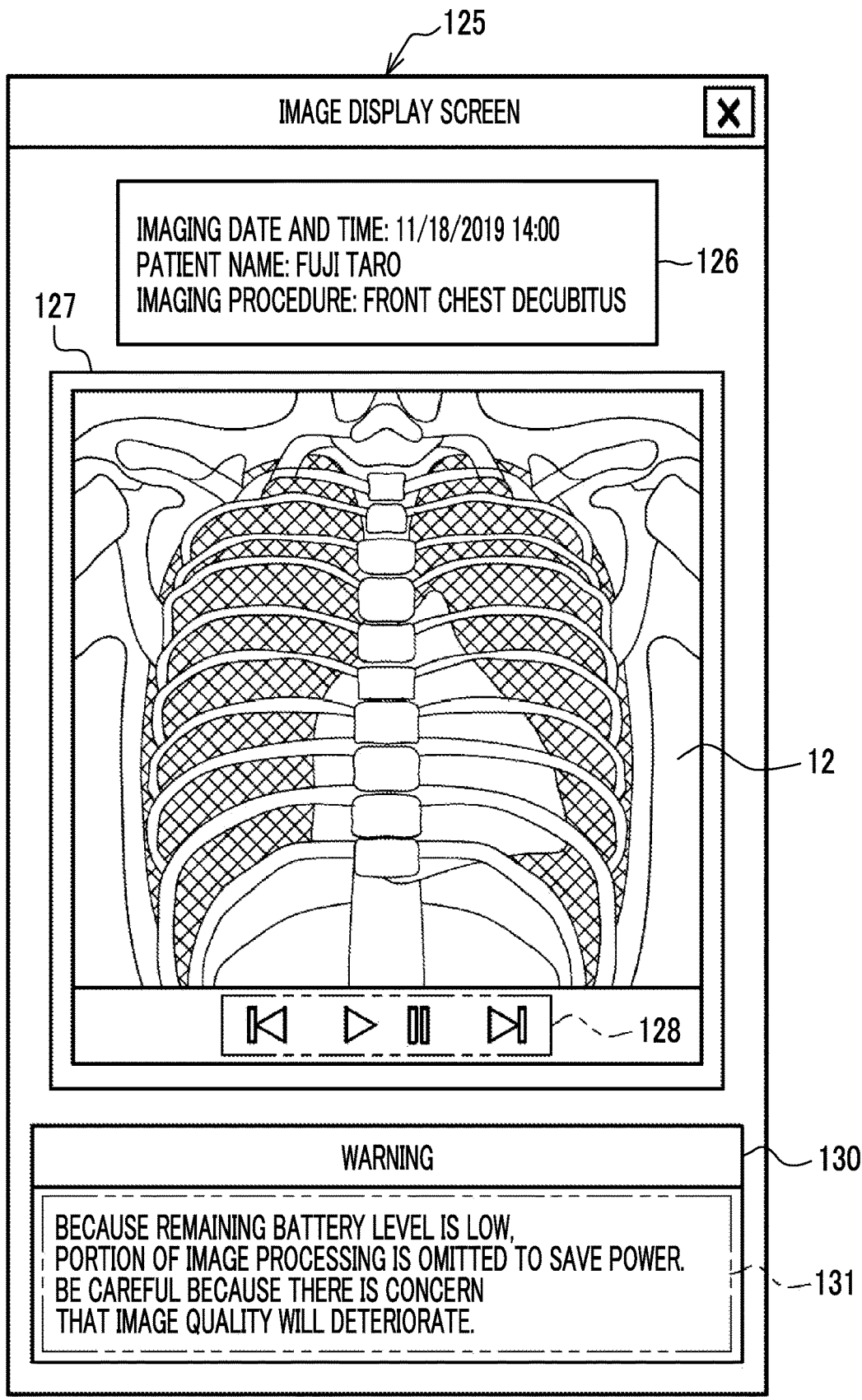
FIG. 16 is a diagram illustrating an image display screen in a case in which the remaining battery level is less than the threshold value.

In FIGS. 15 and 16, an imaging information display frame 126 and an image display frame 127 are provided in the image display screen 125 displayed on the display 43 under the control of the display control unit 86. An imaging date and time, the name of the subject 11 (represented by a "patient name" in FIGS. 15 and 16), and an imaging procedure are displayed in the imaging information display frame 126. The radiographic image 12 is displayed as a moving image in the image display frame 127.

An operation button group 128 is provided below the radiographic image 12 in the image display frame 127. The operation button group 128 includes a reproduction button, a pause button, a frame return button, and a frame advance button for the display of the radiographic image 12 as a moving image.

FIG. 15 illustrates the image display screen 125 in a case in which the remaining battery level 96 is equal to or greater than the threshold value and both the first processing block 100 and the second processing block 101 are operating. In contrast, FIG. 16 illustrates the image display screen 125 in a case in which the remaining battery level 96 is less than the threshold value, the operation of the first processing block 100 is stopped, and only the second processing block 101 is operating.

The image display screen 125 illustrated in FIG. 16 is provided with a warning display frame 130 in addition to the imaging information display frame 126 and the image display frame 127. A warning 131 indicating that the noise suppression process and the visibility improvement process of the first processing block 100 are not performed since the remaining battery level 96 is less than the threshold value and attention is required since there is a concern about the quality of the radiographic image 12 is displayed in the warning display frame 130.

Figure 17:
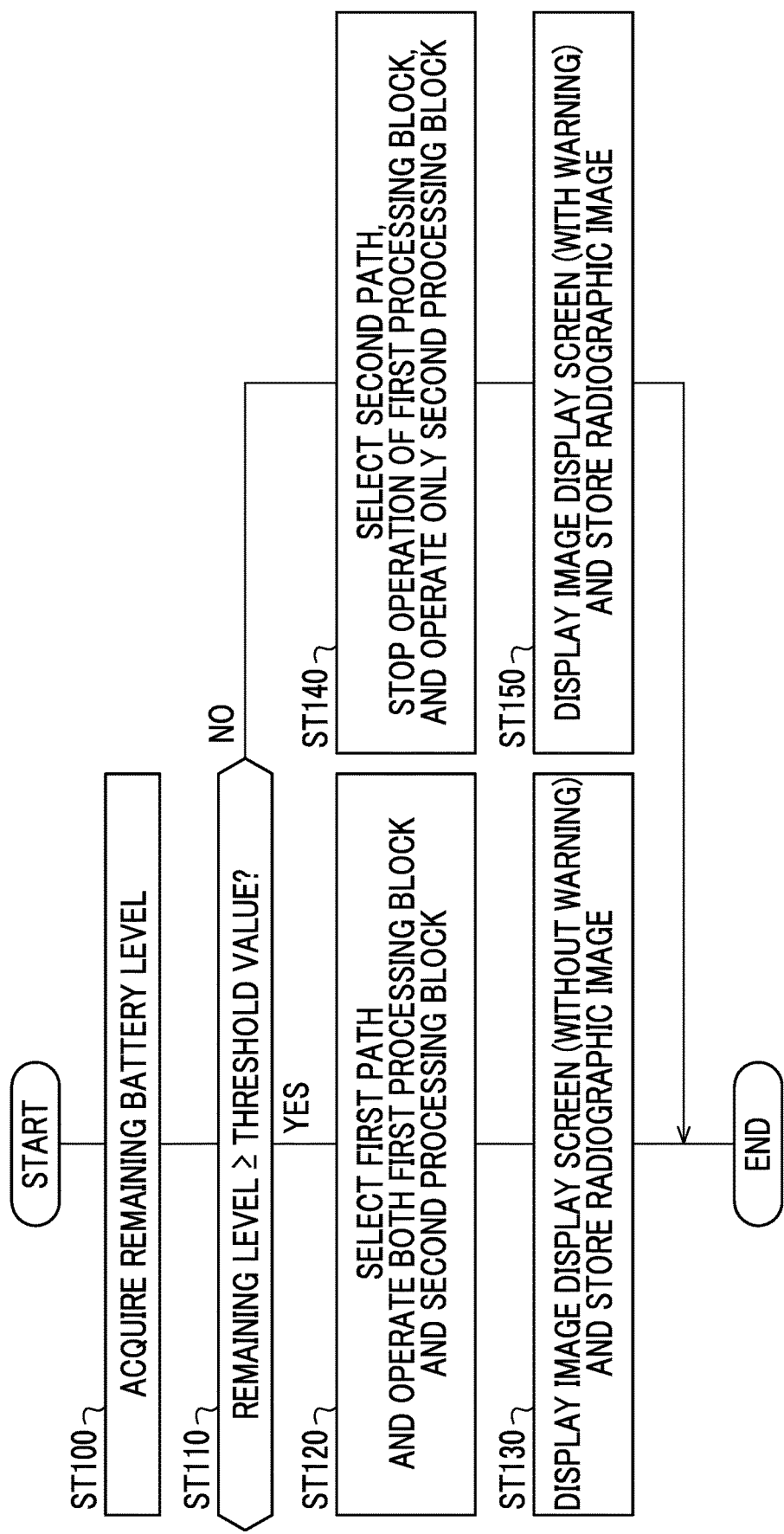
FIG. 17 is a flowchart illustrating a processing procedure of the imaging control device.

Next, the operation of the above-mentioned configuration will be described with reference to a flowchart illustrated in FIG. 17. In a case in which the operation program 80 is started in the imaging control device 42, as illustrated in FIG. 6, the CPU 72 of the imaging control device 42 functions as the irradiation condition acquisition unit 85, the display control unit 86, the RW control unit 87, the remaining level acquisition unit 88, and the operation control unit 89. In addition, the FPGA 73 functions as the radiation source control unit 90, the detector control unit 91, the image acquisition unit 92, and the image processing unit 93.

First, the radiology technician 13 inputs the irradiation conditions 95 through the operation input unit 44 before the capture of a moving image. The irradiation conditions 95 are acquired by the irradiation condition acquisition unit 85 and are output from the irradiation condition acquisition unit 85 to the radiation source control unit 90. The irradiation conditions 95 are set in the voltage generator 41 by the radiation source control unit 90.

In a case in which the radiology technician 13 inputs a command to start the capture of a moving image through the irradiation switch, the moving image capture illustrated in FIG. 7 is started under the set irradiation conditions 95. Specifically, the radiation 10 is intermittently emitted from the radiation source 25 a plurality of times under the control of the radiation source control unit 90. Further, the radiographic image 12 is output from the radiation detector 26 whenever the radiation 10 is emitted under the control of the detector control unit 91. The radiographic image 12 is acquired by the image acquisition unit 92 and is output from the image acquisition unit 92 to the image processing unit 93.

The remaining level acquisition unit 88 acquires the remaining battery level 96 at a predetermined time interval (Step ST100). The remaining battery level 96 is output from the remaining level acquisition unit 88 to the operation control unit 89. Step ST100 is an example of an "acquisition step" according to the technology of the present disclosure.

In a case in which the remaining battery level 96 is equal to or greater than the threshold value (YES in Step ST110), the operation control unit 89 generates the operation control signal 97A having the content that the first path 115 is selected by the first switch 113 and the second switch 114, the power supply state is selected by the third switch 117, and both the first processing block 100 and the second processing block 101 are operated as illustrated in FIG. 13. Then, the operation control signal 97A is output from the operation control unit 89 to the image processing unit 93.

The image processing unit 93 receives the operation control signal 97A and the first path 115 is selected by the first switch 113 and the second switch 114, as illustrated in FIG. 9. In addition, the power supply state is selected by the third switch 117. Then, both the first processing block 100 and the second processing block 101 are operated (Step ST120). The noise suppression process of the noise suppression processing unit 110, the visibility improvement process of the visibility improvement processing unit 111, and the density correction process of the density correction processing unit 112 are performed on the radiographic image 12. The radiographic image 12P subjected to the image processing is output from the image processing unit 93 to the display control unit 86 and the RW control unit 87. Step ST120 is an example of a "first operation control step" according to the technology of the present disclosure.

The display control unit 86 generates the image display screen 125 without the warning display frame 130 illustrated in FIG. 15 on the basis of the radiographic image 12P subjected to the image processing. The image display screen 125 is displayed on the display 43 under the control of the display control unit 86. Further, the RW control unit 87 stores the radiographic image 12P subjected to the image processing in the storage device 70 (Step ST130).

In contrast, in a case in which the remaining battery level 96 is less than the threshold value (NO in Step ST110), the operation control unit 89 generates the operation control signal 97B having the content that the second path 116 is selected by the first switch 113 and the second switch 114, the power supply stop state is selected by the third switch 117, the operation of the first processing block 100 is stopped, and only the second processing block 101 is operated, as illustrated in FIG. 14. Then, the operation control signal 97B is output from the operation control unit 89 to the image processing unit 93.

The image processing unit 93 receives the operation control signal 97B and the second path 116 is selected by the first switch 113 and the second switch 114 as illustrated in FIG. 10. Further, the power supply stop state is selected by the third switch 117. Then, the operation of the first processing block 100 is stopped and only the second processing block 101 is operated (Step ST140). The noise suppression process of the noise suppression processing unit 110 and the visibility improvement process of the visibility improvement processing unit 111 are not performed on the radiographic image 12, and only the density correction process of the density correction processing unit 112 is performed on the radiographic image 12. The radiographic image 12P subjected to only the density correction process is output from the image processing unit 93 to the display control unit 86 and the RW control unit 87. Step ST140 is an example of a "second operation control step" according to the technology of the present disclosure.

The display control unit 86 generates the image display screen 125 with the warning display frame 130 illustrated in FIG. 16 on the basis of the radiographic image 12P subjected to the image processing. The image display screen 125 is displayed on the display 43 under the control of the display control unit 86. Further, the RW control unit 87 stores the radiographic image 12P subjected to the image processing in the storage device 70 (Step ST150).

As described above, the CPU 72 of the imaging control device 42 of the radiography apparatus 2 acquires the remaining battery level 96. Then, in a case in which the remaining battery level 96 is equal to or greater than the threshold value, the CPU 72 performs control to operate both the first processing block 100 that performs the noise suppression process of the noise suppression processing unit 110 and the visibility improvement process of the visibility improvement processing unit 111 as the first image processing and the second processing block 101 that performs the density correction process of the density correction processing unit 112 as the second image processing. In contrast, in a case in which the remaining battery level 96 is less than the threshold value, the CPU 72 performs control to stop the operation of the first processing block 100 and to operate only the second processing block 101.

As described above, the noise suppression process of the noise suppression processing unit 110 and the visibility improvement process of the visibility improvement processing unit 111 are not essential processes for securing the radiographic image 12 that is suitable for observation. In contrast, the density correction process of the density correction processing unit 112 is an essential process for securing the radiographic image 12 that is suitable for observation. Therefore, in a case in which the remaining battery level 96 is less than the threshold value, control to stop the operation of the first processing block 100 and to operate only the second processing block 101 is performed to make the battery 40 last long while securing the radiographic image 12 that is suitable for observation.

The CPU 72 outputs the radiographic image 12 from the radiation detector 26 at the predetermined frame interval FI. As illustrated in FIGS. 11 and 12, the density correction processing unit 112 stabilizes the density of the radiographic image 12 of each frame obtained by capturing a moving image. Therefore, in the moving image capture that consumes more power than the still image capture, it is possible to effectively prevent a reduction in the capacity of the battery 40 and to reduce the concern that the battery 40 will run out and the capture of a moving image will be forced to be stopped. In particular, in many cases, a moving image is captured during surgery as illustrated in FIG. 1. Therefore, it can be said that the effect is more useful in avoiding the situation in which the battery 40 runs out during a treatment in surgery and the capture of a moving image is stopped. Further, it is possible to effectively prevent flicker due to a difference in density in a case in which the radiographic image 12 of each frame obtained by capturing a moving image is displayed as a moving image. Therefore, it is possible to perform a treatment using the treatment tool 120 at ease.

As illustrated in FIG. 16, in a case in which the operation of the first processing block 100 is stopped, the CPU 72 performs control to display information indicating that the noise suppression process and the visibility improvement process are not performed. Therefore, the user can know that there is a concern about the quality of the radiographic image 12 since the noise suppression process and the visibility improvement process are not performed.

As illustrated in FIGS. 9 and 10, the image processing unit 93 has the first path 115 from the radiation detector 26 to the second processing block 101 through the first processing block 100 and the second path 116 from the radiation detector 26 to the second processing block 101 without passing through the first processing block 100. The CPU 72 performs control to select the first path 115 in a case in which the remaining battery level 96 is equal to or greater than the threshold value and performs control to select the second path 116 in a case in which the remaining battery level 96 is less than the threshold value. Therefore, in a case in which the remaining battery level 96 is less than the threshold value, it is possible to avoid the situation in which the radiographic image 12 is input to the first processing block 100 that is not supplied with power and is not operating and meaningless data is output.

In addition, the imaging control device 42 may perform the offset correction process, the sensitivity correction process, and the defective pixel correction process performed by the correction processing circuit 62 of the radiation detector 26.

The density correction processing unit 112 performs the density correction process on the radiographic images 12 of a plurality of frames obtained by capturing a moving image. However, the present disclosure is not limited thereto. The density correction process may be performed on a plurality of radiographic images 12 obtained by capturing the still images of the same subject 11.

The remaining battery level 96 may be displayed on the image display screen 125. Further, the warning 131 may be displayed on a screen different from the image display screen 125 so as to be popped up.

Second Embodiment

In the first embodiment, the supply of power from the battery 40 to the first processing block 100 is stopped to stop the operation of the first processing block 100. However, the present disclosure is not limited thereto. A second embodiment illustrated in FIGS. 18 and 19 may be adopted.

Figure 18:
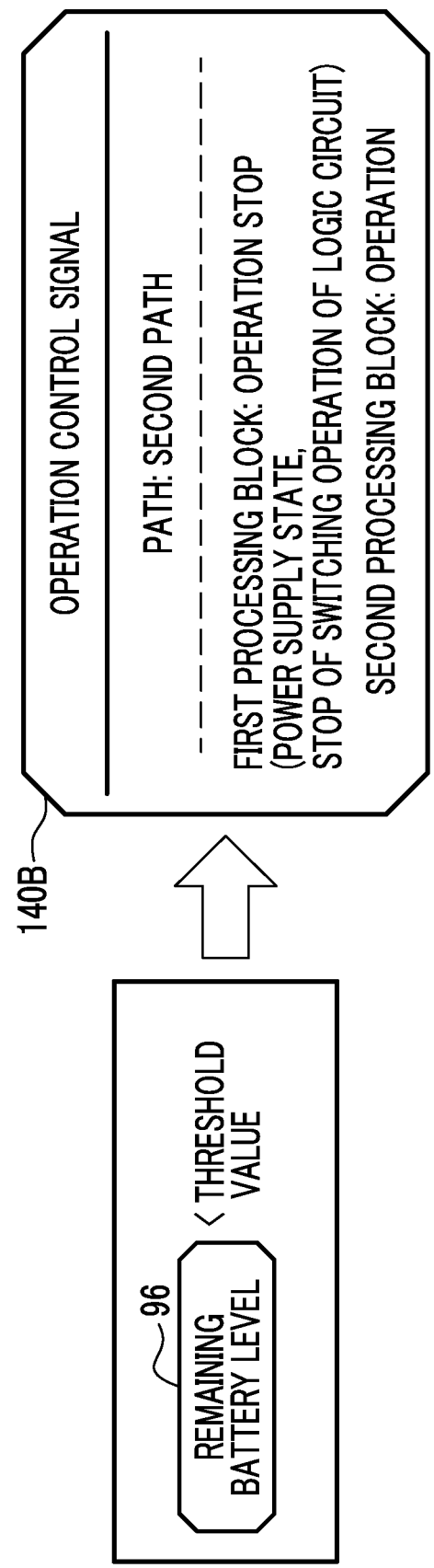
FIG. 18 is a diagram illustrating an operation control signal in a case in which the remaining battery level is less than the threshold value in a second embodiment.

As illustrated in FIG. 18, in the second embodiment, the content of an operation control signal 140B in a case in which the remaining battery level 96 is less than the threshold value is the same as the content of the operation control signal 97B illustrated in FIG. 14 in the first embodiment in that the second path 116 is selected by the first switch 113 and the second switch 114. However, the operation control signal 140B is different from the operation control signal 97B in that, instead of the power supply stop state, the power supply state is selected by the third switch 117 and the switching operation of the logic circuit 102 of the first processing block 100 is stopped. In a case in which the remaining battery level 96 is equal to or greater than the threshold value, the operation control signal 97A illustrated in FIG. 13 in the first embodiment is used.

Figure 19:
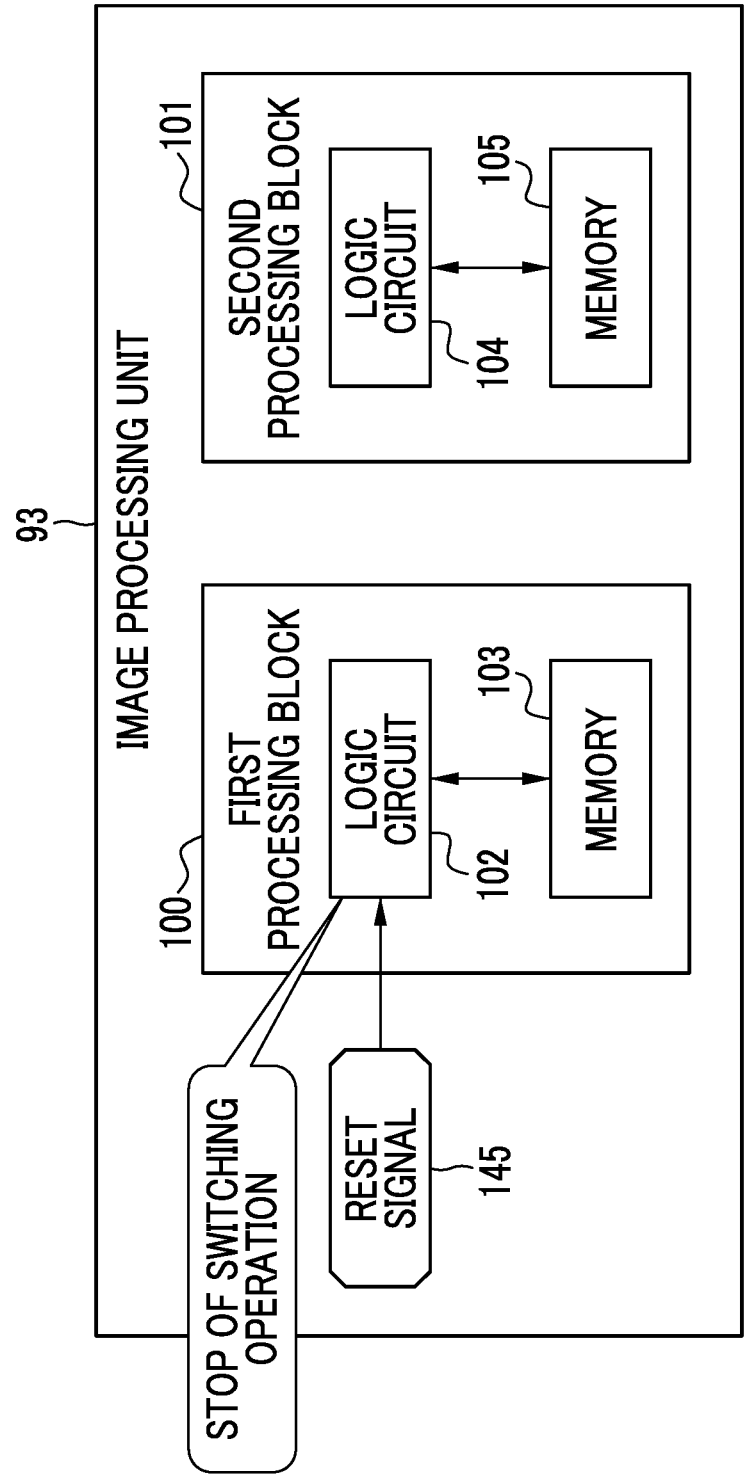
FIG. 19 is a diagram illustrating an aspect in which a switching operation of a logic circuit in a first processing block is stopped to stop the operation of the first processing block.

In a case in which the operation control signal 140B is received, the image processing unit 93 inputs a reset signal 145 to the logic circuit 102 of the first processing block 100 to stop the switching operation of the logic circuit 102, as illustrated in FIG. 19. That is, in the second embodiment, the CPU 72 stops the switching operation of the logic circuit 102 to stop the operation of the first processing block 100 in a case in which the remaining battery level 96 is less than the threshold value.

It is preferable to stop the supply of power from the battery 40 to the first processing block 100 from the viewpoint of preventing a reduction in the capacity of the battery 40 as in the first embodiment. However, it takes a certain amount of time to restart the supply of power to the first processing block 100 and to restart the first processing block 100. In contrast, in an aspect in which the switching operation of the logic circuit 102 is stopped as in the second embodiment, more power is consumed than in the first embodiment, but it is possible to restart the first processing block 100 in a short time.

A configuration may be used in which the radiology technician 13 selects the aspect of stopping the switching operation of the logic circuit 102 in the second embodiment and the aspect of stopping the supply of power from the battery 40 to the first processing block 100 in the first embodiment.

Third Embodiment

In a third embodiment illustrated in FIGS. 20 to 22B, a refresh aspect of the memory 103 of the first processing block 100 is changed depending on the remaining battery level 96.

Figure 20:
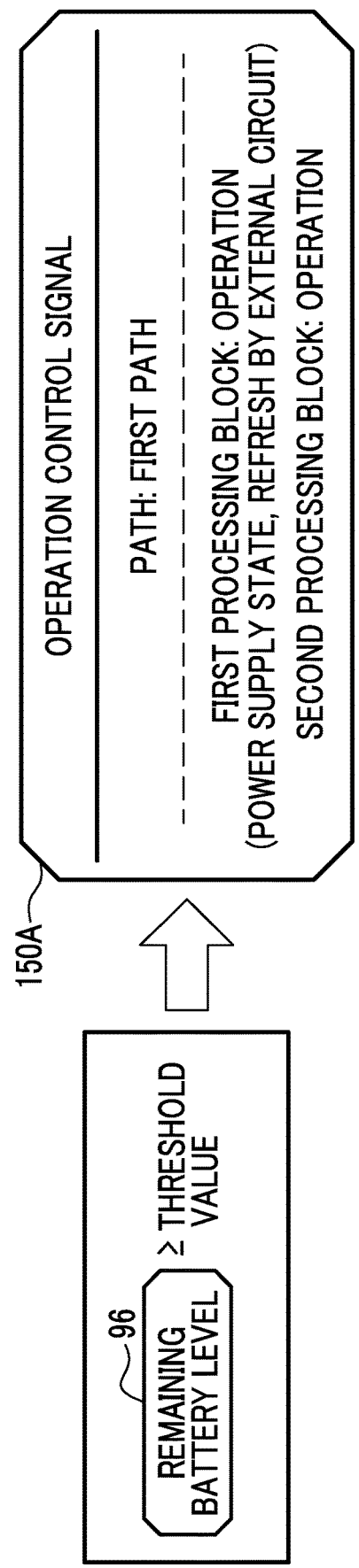
FIG. 20 is a diagram illustrating an operation control signal in a case in which the remaining battery level is equal to or greater than the threshold value in a third embodiment.

As illustrated in FIG. 20, in the third embodiment, an operation control signal 150A in a case in which the remaining battery level 96 is equal to or greater than the threshold value is different from the operation control signal 97A illustrated in FIG. 13 in the first embodiment in that the following content is added. That is, the content that an external circuit refreshes the memory 103 of the first processing block 100 is added.

Figure 21:
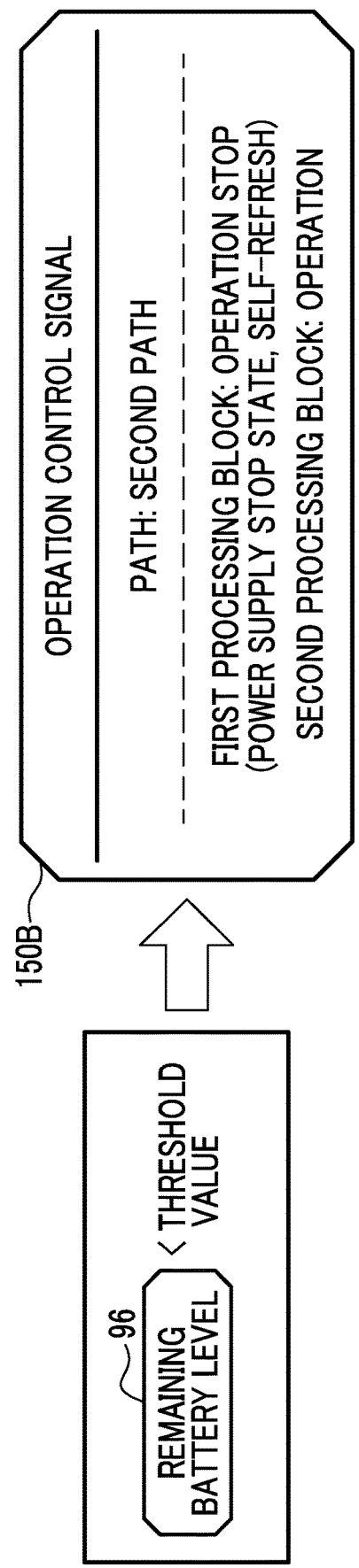
FIG. 21 is a diagram illustrating an operation control signal in a case in which the remaining battery level is less than the threshold value in the third embodiment.

Further, as illustrated in FIG. 21, in the third embodiment, an operation control signal 150B in a case in which the remaining battery level 96 is less than the threshold value is different from the operation control signal 97B illustrated in FIG. 14 in the first embodiment in that the following content is added. That is, the content that the memory 103 refreshes itself in the first processing block 100 is added. The aspect in which the memory 103 refreshes itself is called a self-refresh.

Figure 22A:
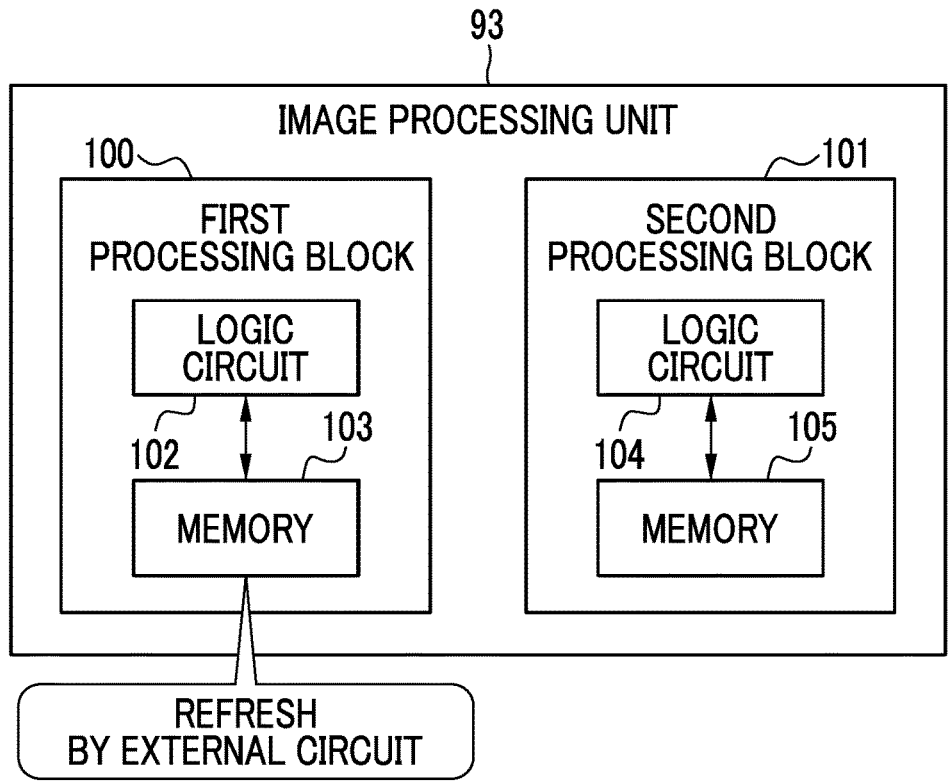
FIGS. 22A and 22B are diagrams illustrating an image processing unit in the third embodiment.
Figure 22B:
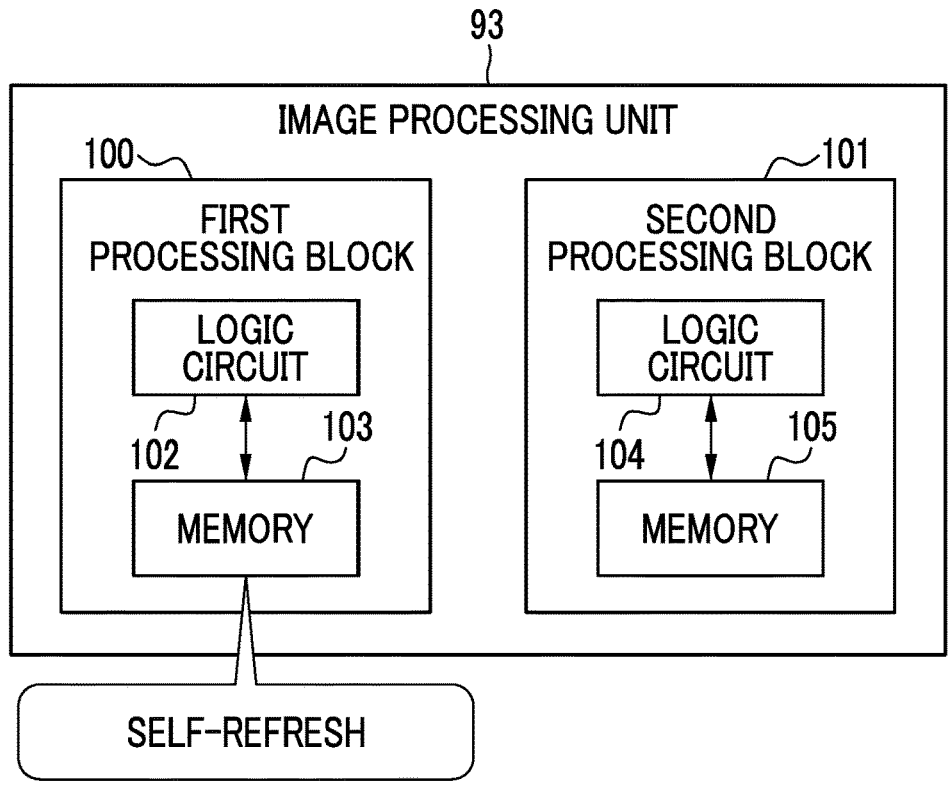

In FIGS. 22A and 22B, FIG. 22A illustrates the image processing unit 93 in a case in which the remaining battery level 96 is equal to or greater than the threshold value and the operation control signal 150A illustrated in FIG. 20 is received, and FIG. 22B illustrates the image processing unit 93 in a case in which the remaining battery level 96 is less than the threshold value and the operation control signal 150B illustrated in FIG. 21 is received. In FIG. 22A, the memory 103 is refreshed by an external circuit. In contrast, in FIG. 22B, the self-refresh is performed. That is, in the third embodiment, the CPU 72 directs the external circuit to refresh the memory 103 in a case in which the remaining battery level 96 is equal to or greater than the threshold value and directs the memory 103 to perform the self-refresh in a case in which the remaining battery level 96 is less than the threshold value.

The self-refresh consumes less power than the refresh by the external circuit. Therefore, in a case in which the remaining battery level 96 is less than the threshold value and the memory 103 performs the self-refresh, it is possible to further prevent a reduction in the capacity of the battery 40 and to further reduce the concern in which the battery 40 will run out and the capture of a moving image will be forced to be stopped.

Fourth Embodiment

Figure 23:
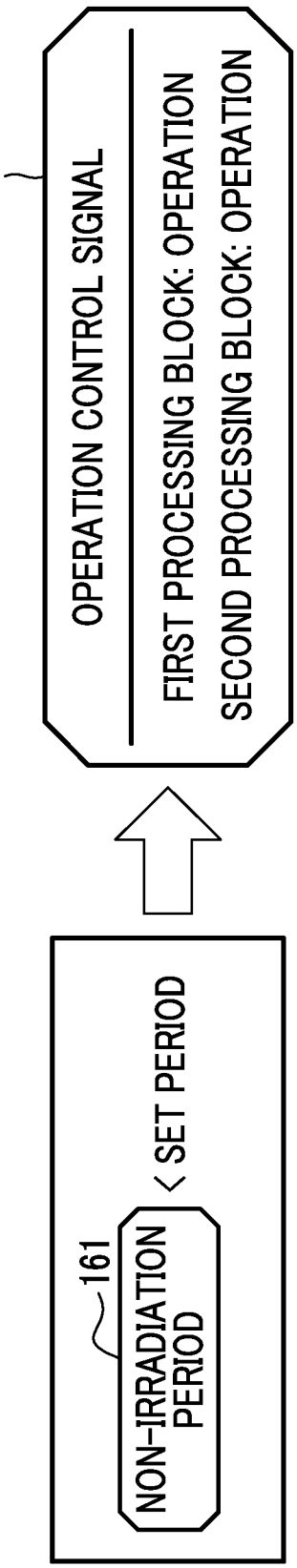
FIG. 23 is a diagram illustrating an operation control signal in a case in which a non-irradiation period is shorter than a set period.
Figure 24:
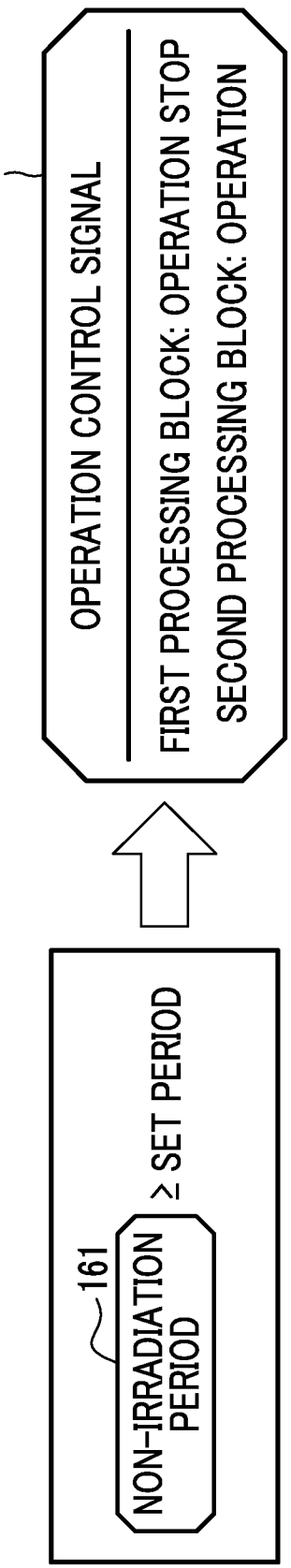
FIG. 24 is a diagram illustrating an operation control signal in a case in which the non-irradiation period is equal to or longer than the set period.
Figure 25:
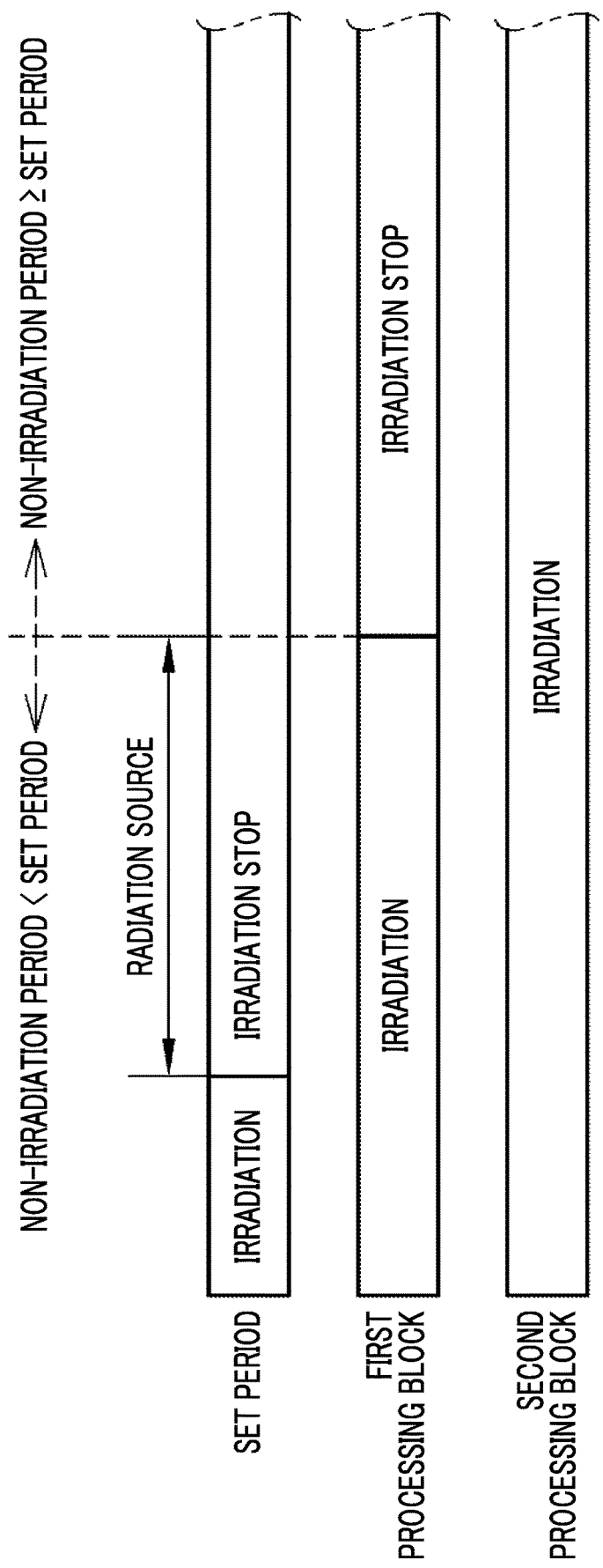
FIG. 25 is a diagram illustrating the operation timing of a radiation source, a first processing block, and a second processing block in a fourth embodiment.

In a fourth embodiment illustrated in FIGS. 23 to 25, the operation of the first processing block 100 and the second processing block 101 is controlled on the basis of a non-irradiation period 161 for which the radiation 10 is not emitted, regardless of the remaining battery level 96.

In the fourth embodiment, the operation control unit 89 outputs an operation control signal 160A illustrated in FIG. 23 or an operation control signal 160B illustrated in FIG. 24 to the image processing unit 93. The content of the operation control signal 160A illustrated in FIG. 23 is that, in a case in which the non-irradiation period 161 is shorter than a predetermined period (hereinafter, referred to as a set period), both the first processing block 100 and the second processing block 101 are operated. In contrast, the content of the operation control signal 160B illustrated in FIG. 24 is that, in a case in which the non-irradiation period 161 is equal to or longer than the set period, the operation of the first processing block 100 is stopped and only the second processing block 101 is operated.

FIG. 25 illustrates the operation timing of the radiation source 25, the first processing block 100, and the second processing block 101 in the fourth embodiment. In a case in which the non-irradiation period 161 is shorter than the set period, both the first processing block 100 and the second processing block 101 are operated. In contrast, in a case in which the non-irradiation period 161 is equal to or longer than the set period, the operation of the first processing block 100 is stopped, and only the second processing block 101 is operated. That is, in the fourth embodiment, the CPU 72 performs control to stop the operation of the first processing block 100 and to operate only the second processing block 101 in a case in which the non-irradiation period 161 is equal to or longer than the set period, regardless of the remaining battery level 96.

As such, in the fourth embodiment, the operation of the first processing block 100 is stopped in a case in which the non-irradiation period 161 is equal to or longer than the set period, that is, in a case in which the radiation 10 is not emitted for a predetermined period. Therefore, it is possible to prevent a reduction in the capacity of the battery 40. Further, the time and effort required to restart the image processing unit 93 are less than that in a case in which not only the operation of the first processing block 100 but also the operation of the second processing block 101 is stopped.

Of course, in a case in which the non-irradiation period 161 is equal to or longer than the set period, not only the operation of the first processing block 100 but also the operation of the second processing block 101 may be stopped, that is, the operation of the image processing unit 93 may be stopped in order to prevent a reduction in the capacity of the battery 40. In this case, it is preferable that the radiation source control unit 90, the detector control unit 91, and the image acquisition unit 92 other than the image processing unit 93 are operated in the FPGA 73. In this case, it is possible to obtain the effect of reducing the time and effort required to restart the FPGA 73, as compared to a case in which the operations of all of the processing units 90 to 93 in the FPGA 73 are stopped.

In the fourth embodiment, either the first path 115 or the second path 116 may be selected in a case in which the non-irradiation period 161 is shorter than the set period and in a case in which the non-irradiation period 161 is equal to or longer than the set period. Further, in the fourth embodiment, any of the aspect of the first embodiment in which the supply of power from the battery 40 to the first processing block 100 is stopped or the aspect of the second embodiment in which the switching operation of the logic circuit 102 is stopped may be adopted as the aspect in which the operation of the first processing block 100 is stopped.

The visibility improvement process may include a process of adjusting the dynamic range of the radiographic image 12, instead of or in addition to the process of highlighting the structure in the subject 11.

In a state in which power is supplied from the battery 40 to the first processing block 100 and the switching operation of the logic circuit 102 in the first processing block 100 is performed, the noise suppression process of the noise suppression processing unit 110 and the visibility improvement process of the visibility improvement processing unit 111 in the first processing block 100 may not be performed. In this case, the operation of the first processing block 100 is also stopped. Then, since the noise suppression process and the visibility improvement process are not performed, the time required for image processing is shortened. As a result, power consumption is reduced.

The first image processing may be any one of the noise suppression process of the noise suppression processing unit 110 or the visibility improvement process of the visibility improvement processing unit 111. Further, the memories 103 and 105 may not be separately prepared for the first processing block 100 and the second processing block 101, respectively, but one memory common to the first processing block 100 and the second processing block 101 may be prepared.

The hardware configuration of the computer forming the imaging control device 42 can be modified in various ways. For example, the imaging control device 42 may be configured by a plurality of computers separated as hardware in order to improve processing capability and reliability. Specifically, the functions of the irradiation condition acquisition unit 85, the radiation source control unit 90, and the detector control unit 91 and the functions of the image acquisition unit 92, the display control unit 86, the RW control unit 87, the remaining level acquisition unit 88, and the operation control unit 89 are distributed to two computers. In this case, the two computers form the imaging control device 42. In addition, the image processing unit 93 is provided in the latter computer in which the image acquisition unit 92 and the like are provided.

As such, the hardware configuration of the computer of the imaging control device 42 can be appropriately changed according to required performances, such as processing capacity, safety, and reliability. Further, not only the hardware but also an application program, such as the operation program 80, may be duplicated or may be dispersively stored in a plurality of storage devices in order to ensure safety and reliability.

In each of the above-described embodiments, for example, the following various processors can be used as a hardware structure of processing units performing various processes, such as the irradiation condition acquisition unit 85, the display control unit 86, the RW control unit 87, the remaining level acquisition unit 88, the operation control unit 89, the radiation source control unit 90, the detector control unit 91, the image acquisition unit 92, and the image processing unit 93. The various processors include, for example, the CPU 72 which is a general-purpose processor executing software to function as various processing units, a PLD, such as the FPGA 73, and a dedicated electric circuit, such as an ASIC.

One processing unit may be configured by one of the various processors or a combination of two or more processors of the same type or different types (for example, a combination of a plurality of FPGAs and a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system on chip (SoC). As such, various processing units are configured by using one or more of the various processors as the hardware structure.

In addition, specifically, an electric circuit (circuitry) obtained by combining circuit elements, such as semiconductor elements, can be used as the hardware structure of the various processors.

The technology of the present disclosure may be appropriately combined with the above-described various embodiments and various modification examples. Further, it is needless to say that the present disclosure is not limited to each of the above-described embodiments and various configurations can be adopted without departing from the scope of the invention. Furthermore, the technology of the present disclosure extends to a storage medium that non-temporarily stores a program, in addition to the program.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions according to the technology of the present disclosure. Therefore, unnecessary portions may be deleted or new elements may be added or replaced in the above descriptions and illustrations without departing from the scope and spirit of the technology of the present disclosure. In addition, the description of, for example, common technical knowledge that does not need to be particularly described to enable the implementation of the technology of the present disclosure is omitted in order to avoid confusion and to facilitate the understanding of portions related to the technology of the present disclosure.

All of the documents, the patent applications, and the technical standards described in the specification are incorporated by reference herein to the same extent as each individual document, each patent application, and each technical standard are specifically and individually stated to be incorporated by reference.

What is claimed is:

1. A radiography apparatus that is driven by power supplied from a battery, the radiography apparatus comprising:
   a radiation source that emits radiation to a subject;
   a radiation detector that receives the radiation transmitted through the subject and outputs a radiographic image; and
   an image processing device that performs image processing on the radiographic image,
   wherein the radiation source, the radiation detector, and the image processing device are integrated,
   the image processing includes first image processing that performs at least one of a noise suppression process suppressing noise of the radiographic image or a visibility improvement process improving visibility of the radiographic image and second image processing that performs a density correction process correcting densities of two or more radiographic images of the same subject which have a time difference therebetween,
   the radiography apparatus includes at least one processor, and
   the processor acquires a remaining level of the battery,
   performs control to operate both a first processing block performing the first image processing and a second processing block performing the second image processing in a case in which the remaining level is equal to or greater than a predetermined threshold value, and
   performs control to stop an operation of the first processing block and to operate only the second processing block in a case in which the remaining level is less than the threshold value.

2. The radiography apparatus according to claim 1, wherein the processor outputs the radiographic image from the radiation detector at a predetermined frame interval, and
   the density correction process is a process that stabilizes the density of the radiographic image of each frame.

3. The radiography apparatus according to claim 1, wherein the processor performs control to display information indicating that the first image processing is not performed in a case in which the operation of the first processing block is stopped.

4. The radiography apparatus according to claim 1, wherein the radiography apparatus has a first path from the radiation detector to the second processing block through the first processing block, and
   a second path from the radiation detector to the second processing block without passing through the first processing block, and
   the processor performs control to select the first path in a case in which the remaining level is equal to or greater than the threshold value and
   performs control to select the second path in a case in which the remaining level is less than the threshold value.

5. The radiography apparatus according to claim 1, wherein, in a case in which the remaining level is less than the threshold value, the processor stops the supply of the power from the battery to the first processing block to stop the operation of the first processing block.

6. The radiography apparatus according to claim 1, wherein the first processing block includes a logic circuit, and
   in a case in which the remaining level is less than the threshold value, the processor stops a switching operation of the logic circuit to stop the operation of the first processing block.

7. The radiography apparatus according to claim 1, wherein the first processing block includes a memory that requires a refresh to replenish charge stored in a memory cell and temporarily stores intermediate data generated by processing,
   the processor directs an external circuit to perform the refresh in a case in which the remaining level is equal to or greater than the threshold value, and
   directs the memory to perform the refresh in a case in which the remaining level is less than the threshold value.

8. The radiography apparatus according to claim 1, wherein, in a case in which the emission of the radiation is not performed for a predetermined period, the processor performs control to stop the operation of the first processing block and to operate only the second processing block, regardless of the remaining level.

9. A method for operating a radiography apparatus that is driven by power supplied from a battery and includes a radiation source that emits radiation to a subject, a radiation detector that receives the radiation transmitted through the subject and outputs a radiographic image, and an image processing device that performs image processing on the radiographic image, the radiation source, the radiation detector, and the image processing device being integrated,
   wherein the image processing includes first image processing that performs at least one of a noise suppression process suppressing noise of the radiographic image or a visibility improvement process improving visibility of the radiographic image and second image processing that performs a density correction process correcting densities of two or more radiographic images of the same subject which have a time difference therebetween, and
   the method comprises: an acquisition step of acquiring a remaining level of the battery;
   a first operation control step of performing control to operate both a first processing block performing the first image processing and a second processing block performing the second image processing in a case in which the remaining level is equal to or greater than a predetermined threshold value; and a second operation control step of performing control to stop an operation of the first processing block and to operate only the second processing block in a case in which the remaining level is less than the threshold value.

10. A non-transitory computer-readable storage medium storing a program for operating a radiography apparatus that is driven by power supplied from a battery and includes a radiation source that emits radiation to a subject, a radiation detector that receives the radiation transmitted through the subject and outputs a radiographic image, and an image processing device that performs image processing on the radiographic image, the radiation source, the radiation detector, and the image processing device being integrated, wherein the image processing includes first image processing that performs at least one of a noise suppression process suppressing noise of the radiographic image or a visibility improvement process improving visibility of the radiographic image and second image processing that performs a density correction process correcting densities of two or more radiographic images which include the same object and have a time difference therebetween, and the program causes a computer to function as: an acquisition unit that acquires a remaining level of the battery; and an operation control unit that performs control to operate both a first processing block performing the first image processing and a second processing block performing the second image processing in a case in which the remaining level is equal to or greater than a predetermined threshold value, and performs control to stop an operation of the first processing block and to operate only the second processing block in a case in which the remaining level is less than the threshold value.

* * * * *